United States Patent
Lu et al.

(10) Patent No.: US 9,879,278 B2
(45) Date of Patent: Jan. 30, 2018

(54) NON-VIRAL EPISOMAL SUICIDE CONSTRUCT

(71) Applicant: WAKE FOREST UNIVERSITY HEALTH SCIENCES, Winston Salem, NC (US)

(72) Inventors: Baisong Lu, Winston Salem, NC (US); Qingguo Zhao, Winston Salem, NC (US); James Yoo, Winston Salem, NC (US); Anthony Atala, Winston Salem, NC (US)

(73) Assignee: Wake Forest University Health Sciences, Winston Salem, NC (US)

( * ) Notice: Subject to any disclaimer, the term of this patent is extended or adjusted under 35 U.S.C. 154(b) by 0 days.

(21) Appl. No.: 14/382,816

(22) PCT Filed: Feb. 27, 2013

(86) PCT No.: PCT/US2013/027868
§ 371 (c)(1),
(2) Date: Sep. 4, 2014

(87) PCT Pub. No.: WO2013/134015
PCT Pub. Date: Sep. 12, 2013

(65) Prior Publication Data
US 2015/0079682 A1    Mar. 19, 2015

Related U.S. Application Data

(60) Provisional application No. 61/606,664, filed on Mar. 5, 2012.

(51) Int. Cl.
C12N 15/85 (2006.01)
(52) U.S. Cl.
CPC .......... *C12N 15/85* (2013.01); *C12N 2800/40* (2013.01); *C12N 2840/007* (2013.01)
(58) Field of Classification Search
None
See application file for complete search history.

(56) References Cited

U.S. PATENT DOCUMENTS

| | | | |
|---|---|---|---|
| 6,576,464 B2 | 6/2003 | Gold et al. | |
| 7,371,542 B2 | 5/2008 | Ivanova et al. | |
| 2002/0107869 A1* | 8/2002 | Leroy | A61K 9/0024 |
| 2008/0299582 A1 | 12/2008 | Mandalam et al. | |
| 2011/0061117 A1 | 3/2011 | Mermod et al. | |
| 2011/0104125 A1* | 5/2011 | Yu | A61K 35/545 424/93.7 |

OTHER PUBLICATIONS

Stehle et al., Exploiting a minimal system to study the epigenetic control of DNA replication: the interplay between transcription and replication; Chromosome Research, vol. 11, pp. 413-421, 2003.*
Jenke et al., Nuclear scaffold/matrix attached region modules linked to a transcription unit are sufficient for replication and maintenance of a mammalian episome; PNAS, vol. 101, No. 31, pp. 11322-11327, 2004.*
Adamson, A.D. et al., "Novel Approaches to in vitro Transgenesis," Journal of Endocrinology, vol. 208, pp. 193-206, 2011.
Argyros, O. et al., "Persistent Episomal Transgene Expression in Liver Following Delivery of a Scaffold/Matrix Attachment Region Containing Non-viral Vector," Gene Therapy, vol. 15, pp. 1593-1605, 2008.
Haase, R. et al., "pEPito: a Significantly Improved Non-viral Episomal Expression Vector for Mammalian Cells," BMC Biothechnology, vol. 10:20, pp. 1-14, 2010.
Hara, A. et al., "Neuron-Like Differentiation and Selective Ablation of Undifferentiated Embryonic Stem Cells Containing Suicide Gene with Oct-4 Promoter," Stem Cells and Development, vol. 17, pp. 619-628, 2008.
Lufino, M. M.P. et al., "An S/MAR based Infectious Episomal Genomic DNA Expression Vector Provides Long-term Regulated Functional Complementation of LDLR Deficiency," Nucleic Acids Research, vol. 35, No. 15, pp. 1-10, 2007.
Papapetrou, E.P. et al., "Gene Transfer into Human Hematopoietic Progenitor Cells with an Episomal Vector Carrying an S/MAR Element," Gene Therapy, vol. 13, pp. 40-51, 2006.
Tessadori, F. et al., "Stable S/MAR-based Episomal Vectors are Regulated at the Chromatin Level," Chromosome Res., vol. 18, pp. 757-775, 2010.
Wong, S.P. et al., "Non-viral S/MAR Vectors Replicate Episomally in vivo when Provided with a Selective Advantage," Gene Therapy, vol. 18, pp. 82-87, 2011.
International Search Report and Written Opinion dated May 10, 2013, for International Application No. PCT/US2013/027868, filed Feb. 27, 2013.

* cited by examiner

*Primary Examiner* — Addison D Ault
(74) *Attorney, Agent, or Firm* — Saul Ewing Arnstein & Lehr LLP; Kathryn Doyle

(57) ABSTRACT

The invention includes compositions and methods for the selective expression of a target gene in a subset of cells. In certain embodiments, the present invention includes a construct comprising a first nucleic acid sequence comprising an episomal maintenance element and a second nucleic acid sequence comprising a target gene wherein the expression of the episomal maintenance element is regulated by a constitutive promoter and the expression of the target gene is regulated by a non-constitutive promoter. The construct is able to maintain episomal state, no matter whether the target gene is expressed in the cell.

4 Claims, 8 Drawing Sheets

SEQUENCE LISTING

<160> NUMBER OF SEQ ID NOS: 14

<210> SEQ ID NO 1
<211> LENGTH: 36
<212> TYPE: DNA
<213> ORGANISM: Artificial sequence
<220> FEATURE:
<223> OTHER INFORMATION: Chemically synthesized

<400> SEQUENCE: 1
gagaccaggt cgtgaggctc cggtgcccgt cagtgg                           36

<210> SEQ ID NO 2
<211> LENGTH: 32
<212> TYPE: DNA

```
<213> ORGANISM: Artificial sequence
<220> FEATURE:
<223> OTHER INFORMATION: Chemically synthesized

<400> SEQUENCE: 2
atacccgggc acgacacctg aaatggaaga aa                                    32

<210> SEQ ID NO 3
<211> LENGTH: 36
<212> TYPE: DNA
<213> ORGANISM: Artificial sequence
<220> FEATURE:
<223> OTHER INFORMATION: Chemically synthesized

<400> SEQUENCE: 3
actccgggag atctaaataa acttataaat tgtgag                                36

<210> SEQ ID NO 4
<211> LENGTH: 43
<212> TYPE: DNA
<213> ORGANISM: Artificial sequence
<220> FEATURE:
<223> OTHER INFORMATION: Chemically synthesized

<400> SEQUENCE: 4
actccgggag aattctatca aatatttaaa gaaaaaaaaa ttg                        43

<210> SEQ ID NO 5
<211> LENGTH: 34
<212> TYPE: DNA
<213> ORGANISM: Artificial sequence
<220> FEATURE:
<223> OTHER INFORMATION: Chemically synthesized

<400> SEQUENCE: 5
acaagatcta ccatggcttc gtacccctgc catc                                  34

<210> SEQ ID NO 6
<211> LENGTH: 30
<212> TYPE: DNA
<213> ORGANISM: Artificial sequence
<220> FEATURE:
<223> OTHER INFORMATION: Chemically synthesized

<400> SEQUENCE: 6
acggtacctc agttagcctc ccccatctcc                                       30

<210> SEQ ID NO 7
<211> LENGTH: 21
<212> TYPE: DNA
<213> ORGANISM: Artificial sequence
<220> FEATURE:
<223> OTHER INFORMATION: Chemically synthesized

<400> SEQUENCE: 7
tgaaggtcgg agtcaacgga t                                                21

<210> SEQ ID NO 8
<211> LENGTH: 21
<212> TYPE: DNA
<213> ORGANISM: Artificial sequence
<220> FEATURE:
<223> OTHER INFORMATION: Chemically synthesized

<400> SEQUENCE: 8
cctggaagat ggtgatggga t                                                21
```

```
<210> SEQ ID NO 9
<211> LENGTH: 20
<212> TYPE: DNA
<213> ORGANISM: Artificial sequence
<220> FEATURE:
<223> OTHER INFORMATION: Chemically synthesized

<400> SEQUENCE: 9
ccgagccgat gacttactgg                                            20

<210> SEQ ID NO 10
<211> LENGTH: 20
<212> TYPE: DNA
<213> ORGANISM: Artificial sequence
<220> FEATURE:
<223> OTHER INFORMATION: Chemically synthesized

<400> SEQUENCE: 10
gtcgaagatg agggtgaggg                                            20

<210> SEQ ID NO 11
<211> LENGTH: 20
<212> TYPE: DNA
<213> ORGANISM: Artificial sequence
<220> FEATURE:
<223> OTHER INFORMATION: Chemically synthesized

<400> SEQUENCE: 11
actgggcaca acagacaatc                                            20

<210> SEQ ID NO 12
<211> LENGTH: 24
<212> TYPE: DNA
<213> ORGANISM: Artificial sequence
<220> FEATURE:
<223> OTHER INFORMATION: Chemically synthesized

<400> SEQUENCE: 12
tggaattttt ttgtgtgtat ggta                                       24

<210> SEQ ID NO 13
<211> LENGTH: 20
<212> TYPE: DNA
<213> ORGANISM: Artificial sequence
<220> FEATURE:
<223> OTHER INFORMATION: Chemically synthesized

<400> SEQUENCE: 13
gcctcacgat ccttctgacc                                            20

<210> SEQ ID NO 14
<211> LENGTH: 20
<212> TYPE: DNA
<213> ORGANISM: Artificial sequence
<220> FEATURE:
<223> OTHER INFORMATION: Chemically synthesized

<400> SEQUENCE: 14
aacccagctc acgttcccta                                            20
```

NON-VIRAL EPISOMAL SUICIDE CONSTRUCT

CROSS-REFERENCE TO RELATED APPLICATIONS

The present application is a 35 U.S.C. § 371 national phase application of, and claims priority to, PCT Application No. PCT/US13/27868, filed Feb. 27, 2013, which claims priority under 35 U.S.C. § 119(e) to U.S. Provisional Patent Application No. 61/606,664, filed Mar. 5, 2012, all of which applications are incorporated herein by reference in their entireties.

STATEMENT REGARDING FEDERALLY SPONSORED RESEARCH OR DEVELOPMENT

This invention was made with government support under W81XWH-07-1-0718 awarded by Department of Defense. The government has certain rights in the invention.

BACKGROUND OF THE INVENTION

Pluripotent human embryonic stem cells and induced pluripotent stem cells provide limitless cell sources for tissue regeneration (Thomson et al., 1998. Science 282: 1145-7; Okita al., 2007, Nature 448:313-7; Takahashi et al., 2006, Cell 126:663-76; Yu et al, 2007, Science 318:1917-20). However, both confer a risk of forming tumors, which must be addressed before their clinical applications are feasible. While in most cases embryonic stem cells and induced pluripotent stem cells will be differentiated into target cells before they are transplanted to patients, the risk of tumor formation is still significant, since residual pluripotent stem cells will remain even after selection based on cell surface markers. Several groups observed teratoma formation after transplantation of differentiated cells from pluripotent stem cells, due to the presence of a low percentage of undifferentiated pluripotent stem cells (Hentze et al., 2009, Stem Cell Res 2:198-210; Xu et al., 2008, Cytotherapy 10:376-89; Duinsbergen et al., 2009, Ann N Y Acad Sci 1176:197-204). Even though 100% of the stem cells are differentiated, in vivo dedifferentiation into pluripotent stem cells is still possible (Brawley et al., 2004, Science 304: 1331-4). Thus, eliminating residual pluripotent stem cells from differentiated cells in vitro and in vivo will reduce the risk of tumor formation and is highly desirable (Kiuru et al., 2009, Cell Stem Cell 4:289-300).

Genetic modification of pluripotent stem cells by suicide genes has been explored to reduce the risk of tumorigenicity. Teratomas formed by embryonic stem cells constitutively expressing the herpes simplex virus thymidine kinase (tk) gene were inhibited by ganciclovir delivery (Schuldiner et al., 2003, Stem Cells 21:257-65; Cao et al., 2006, Circulation 113:1005-14; Jung et al., 2007, Hum Gene Ther 18:1182-92). The pluripotent stem cell-specific OCT4 or NANOG promoter was subsequently used to selectively remove undifferentiated cells from differentiated cells (Naujok et al., 2010, Stem Cell Rev 6:450-61; Hara et al., 2008, Stem Cells Dev 17:619-27; Cheng et al., 2012, Biomaterials 33:3195-204). Other toxic proteins, such as α-1,3-galactosyltransferase and inducible caspase-1, have also been tested to eliminate malignant cells (Hewitt et al., 2007, Stem Cells 25(1):10-8; Wang et al., 2012, Stem Cells 30:169-79). In all these studies, transgenes were integrated into the genome by plasmid or lentiviral integration. This again raises safety concerns due to the possibility of inactivation of tumor suppressor genes or activation of oncogenes (Nusse et al., 1984, Nature 307:131-6). In addition, integrated genes are subject to position effects and silencing (Ellis, 2005, Hum Gene Ther 16:1241-6), making their expression unreliable and unpredictable. Efforts are being made to identify and validate genomic safe harbors for transgene integration to minimize the risks described above (Sadelain et al., 2012, Nat Rev Cancer 12:51-8).

Plasmid vectors containing the scaffold/matrix attached regions (S/MAR) of the human interferon-β gene can maintain their state as episomal DNA in cells of various species, and the plasmid DNA replicates during cell division if the S/MAR sequence is transcribed (piechaczek et al., 1999, Nucleic Acids Res 27:426-8; Stehle et al., 2003, Chromosome Res 11:413-21; Manzini et al., 2006, Proc Natl Acad Sci USA 103:17672-7; Jenke et al., 2004, Proc Natl Acad Sci USA 101:11322-7). The vector replicates once per cell cycle during early S-phase, with the origin recognition complex assembled at various regions on the vector DNA (Schaarschmidt et al., 2004, EMBO J. 23:191-201). The origin recognition complex stably interacts with metaphase chromosomes, which leads to stable episomal maintenance (Baiker et al., 2000, Nat Cell Biol 2:182-4):

Since S/MAR-based vectors do not integrate into the genome of mammalian cells and mediate long-term acne transfer, they should carry reduced risks of insertional mutagenesis, silencing and variegation. However, in currently available S/MAR-based vectors, the S/MAR sequence is transcribed by the same promoter driving the expression of target genes, so that they can only maintain an episomal state in cells expressing the target gene.

Thus, there is a need in the art for an S/MAR based construct to maintain its long term episomal state in all cells, while expressing a target gene only in a subset of cells. The present invention satisfies this need.

SUMMARY OF THE INVENTION

The invention provides a composition comprising a first nucleic acid sequence comprising an episomal maintenance element and a second nucleic acid sequence comprising a target gene, wherein the expression of the episomal maintenance element is regulated by a constitutive promoter and the expression of the target gene is regulated by a non-constitutive promoter.

In one embodiment, the episomal maintenance element is S/MAR.

In one embodiment, the non-constitutive promoter is selected from the group consisting of an inducible promoter, a cell-type specific promoter, and a tumor specific promoter.

In one embodiment, when the target gene is expressed in a cell, the cell is susceptible for cell death.

In one embodiment, the target gene encodes thymidine kinase (TK).

In one embodiment, the cell-type specific promoter is an undifferentiated stem cell specific promoter.

In one embodiment, the undifferentiated stem cell specific promoter is selected from the group consisting of OCT4, hTERT, and NANOG.

In one embodiment, the episomal maintenance element provides long term episomal maintenance of the composition in an entire cell population, and the non-constitutive promoter provides expression of the target gene in a subset of cells of the entire cell population.

The invention also provides a method of providing long term episomal maintenance of a composition comprising a target gene in a cell population while inducing expression of the target gene in a subset of cells of the cell population. In one embodiment, the method comprises administering to a cell population a composition comprising a first nucleic acid sequence comprising an episomal maintenance element and a second nucleic acid sequence comprising a target gene, wherein the expression of the episomal maintenance element is regulated by a constitutive promoter and the expression of the target gene is regulated by a non-constitutive promoter.

The present invention also provides a method of eliminating undifferentiated stem cells from a cell population comprising administering to a cell population a composition comprising a first nucleic acid sequence comprising an episomal maintenance element and a second nucleic acid sequence comprising a target gene, wherein the expression of the episomal maintenance element is regulated by a constitutive promoter and the expression of the target gene is regulated by undifferentiated stein cell specific promoter, further wherein the expression of the target gene induces susceptibility to cell death.

In one embodiment, the episomal maintenance element is S/MAR.

In one embodiment, the undifferentiated stem cell specific promoter is selected from the group consisting of OCT4, hTERT, and NANOG.

In one embodiment, the target gene encodes viral thymidine kinase, and wherein the method further comprises the administration of ganciclovir to the cell population.

In one embodiment, the episomal maintenance element provides long term episomal maintenance of the composition in the entire cell population, and wherein the undifferentiated stem cell specific promoter provides expression of the target gene only in the undifferentiated stem cells that exist or appear in the cell population.

The invention provides a method of reducing or preventing tumor formation in a subject receiving a transplant of a stem cell-derived cell population comprising administering to the cell population a composition comprising a first nucleic acid sequence comprising an episomal maintenance element and a second nucleic acid sequence comprising a target gene, wherein the expression of the episomal maintenance element is regulated by a constitutive promoter and the expression of the target gene is regulated by undifferentiated stem cell specific promoter, further wherein the expression of the target gene induces susceptibility to cell death.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIGS. 1A through 1G, depicts maps, graphs, and images related to the designing of episomal plasmid pS/MAR-GFP2. FIG. 1A: Map of the prototype episomal construct pEPI-eGFP FIG. 1B: Map of pS/MAR-GFP1. The S/MAR sequence was downstream of the SV40-Neo" cassette. FIG. 1C: Map of pS/MAR-GFP2. The human EF1α promoter was used to drive the transcription of the S/MAR sequence and the GFP gene. FIG. 1D: Percentage of GFP-positive cells after transfection without G418 selection. Mean±SEM from 4 independent transfections are presented. No difference was observed between the two plasmids. FIG. 1E: More GFP-positive colonies were formed in cells transfected with pS/MAR-GFP2. Cells were cultured without G418 selection and colony numbers were counted under 10× objective 20 days after transfection. Mean SEM from 40 random fields (10 fields from each of 4 independent transfections) is presented. ***, $p<0.0001$. FIG. 1F: High expression of GFP in colonies formed by pS/MAR-GFP2 transfection. Pictures were taken 20 days after transfection without selection. Scale bar: 100 μm. FIG. 1G: Detection of episomal pS/MAR-GFP2 DNA by Southern blotting, "N" indicates DNA isolated by the Hirt method from untransfected CHO-K1 cells, used as a negative control. "P" indicates 10 pg pS/MAR-GFP2 DNA isolated from E. coli, used as a positive control. T1-T4 were DNA isolated from pS/MAR-GFP2-derived CHO-K1 clones by the HIRT method. All DNA samples were digested with BamHI before electrophoresis.

FIGS. 2A, 2B, and 2C, depicts graphs and an image showing stable and high gene expression of pS/MAR-GFP2-derived CHO-K1 colonies after G418 withdrawal. FIG. 2A: pS/MAR-GFP2 colonies showed a high and stable percentage of GFP-positive cells after G418 withdrawal. Percentages of GFP-positive cells were analyzed by flow cytometry. Means±SEM of 8 pS/MAR-GFP2 subclones and 9 pEPI-eGFP subclones are presented. FIG. 2B: pS/MAR-GFP2 clones showed higher average fluorescence intensity (geometric means from flow cytometry analysis) than pEPI-eGFP clones. Means±SEM of 8 pS/MAR-GFP2 subclones and 9 pEPI-eGFP subclones are presented. FIG. 2C: Fluorescent microscopy also showed higher GFP expression from pS/MAR-GFP2 cells than from pEPI-eGFP cells 39 days after G418 withdrawal. Scale bar: 50 μm #, $P<0.01$, by Bonferroni post-tests following ANOVA.

FIGS. 3A through 3F, depicts maps, images, and graphs related to the pSuicide maintained episomal state and specifically killed pluripotent stem cells in the presence of ganciclovir. FIG. 3A: Map of pSuicide for pluripotent stem cell-specific expression of HSV tk gene. A 5-kb human OCT4 promoter was used to control the transcription of tk gene. FIG. 3B: Detection of episomal pSuicide DNA by Southern blotting. P indicates 10 pg pSuicide plasmid DNA extracted from E. coli as a positive control. T1 and T2 indicate test DNA isolated from NCCIT (pSuicide) clones by the HIRT method. N indicates similarly isolated DNA from NCCIT cells. All DNA samples were digested with EcoRV. The right blot was from another Southern blotting experiment with a different batch of EcoRV digested DNA. FIG. 3C: Detecting S/MAR transcripts by RT-PCR. The forward primer was from the neomycin-resistant gene and the reverse primer was from S/MAR, ensuring detection of only S/MAR transcribed from the pSuicide plasmid. RT: reverse transcriptase. FIG. 3D: Eliminating residual pluripotent stem cells from differentiated NCCIT (pSuicide) cells by ganciclovir. Ganciclovir treatment eliminated OCT4-positive cells in NCCIT/Suicide cells but not in NCCIT cells. NCCIT and NCCIT (pSuicide) cells were induced to differentiate by retinoic acid (RA). Nuclei of all cells were stained blue with DAPI; pluripotent cells were stained red with anti-OCT4A antibody and Texas Red-conjugated secondary antibody. Scale bar: 100 μm. FIG. 3E: Western blotting analysis of OCT4 expression after RA-induced differentiation and ganciclovir treatment. β-Actin was used as loading control. FIG. 3F: Flow cytometry analysis of OCT4-positive cells in RA- and ganciclovir-treated cells. Darkest curve in each graph: isotype control stained cells, showing the positions of OCT4-negative cells. Other curves:

OCT4A antibody stained cells after indicated treatments. Numbers indicate percentage of OCT4-positive cells. The lower limits for MI (OCT4-positive cells) were defined so that the percentage of OCT4-positive cells in isotype control stained cells was near 0.5%. FL4-H: The fluorescent intensity of Texas Red.

Figure 4:
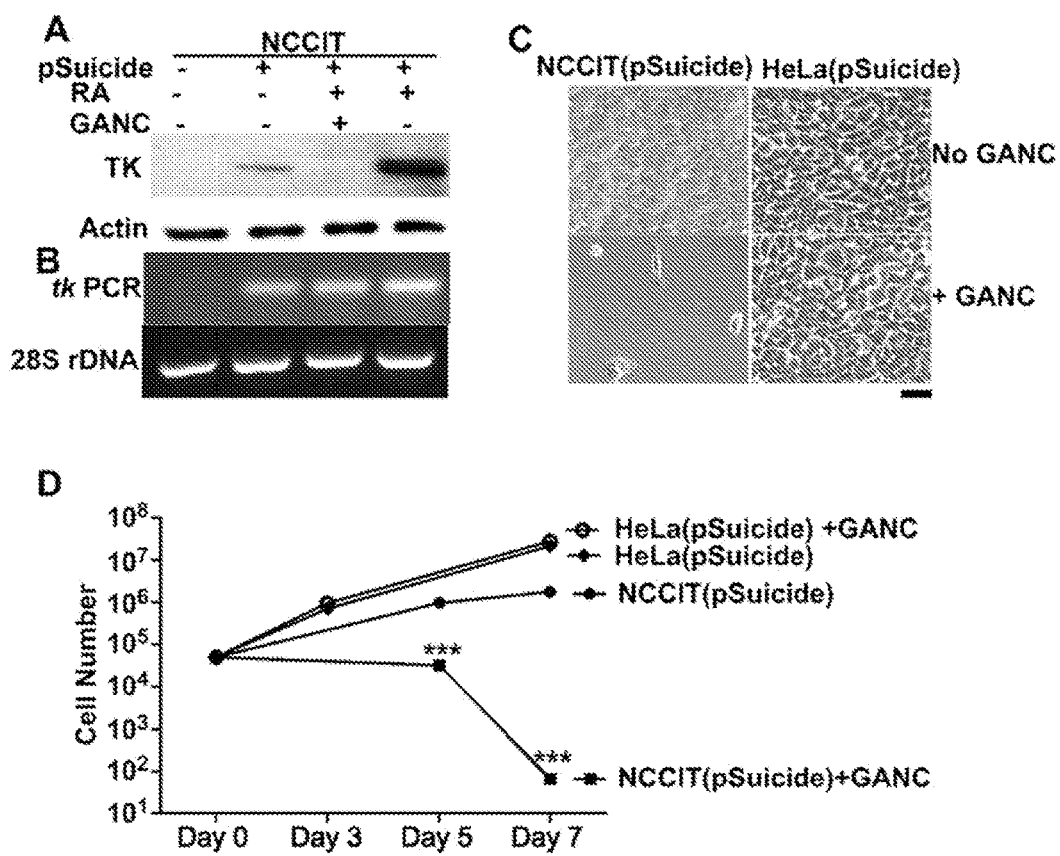

FIG. 4, comprising FIGS. 4A through 4D, depicts images and graphs related to thymidine expression and different effects of ganciclovir on pSuicide-modified cells. FIG. 4A: Expression of thymidine kinase in NCCIT (pSuicide) cells. Cell lysates were analyzed by Western blotting with anti-thymidine kinase and anti-β actin antibodies. FIG. 4B: Detection of pSuicide DNA in NCCIT (pSuicide) cells. Primers specific for HSV tk DNA were used in PCR amplification using total DNA as the templates. Primers recognizing both human and mouse 28S rDNA were used for DNA input control. Sample order was the same as in FIG. 4A. FIG. 4C: Ganciclovir treatment killed NCCIT (pSuicide) cells but not HeLa (pSuicide) cells. Cells were treated with 2 µmol/L ganciclovir for 7 days before pictures were taken. Scale bar: 20 µm. FIG. 4D: Ganciclovir treatment affected the proliferation of NCCIT (pSuicide) cells but not HeLa (pSuicide) cells. Mean±SEM of three independent assays is presented. ***, P<0.0001 between NCCIT (pSuicide) cells with and without ganciclovir treatment, by Bonferroni post-tests following ANOVA.

Figure 5:
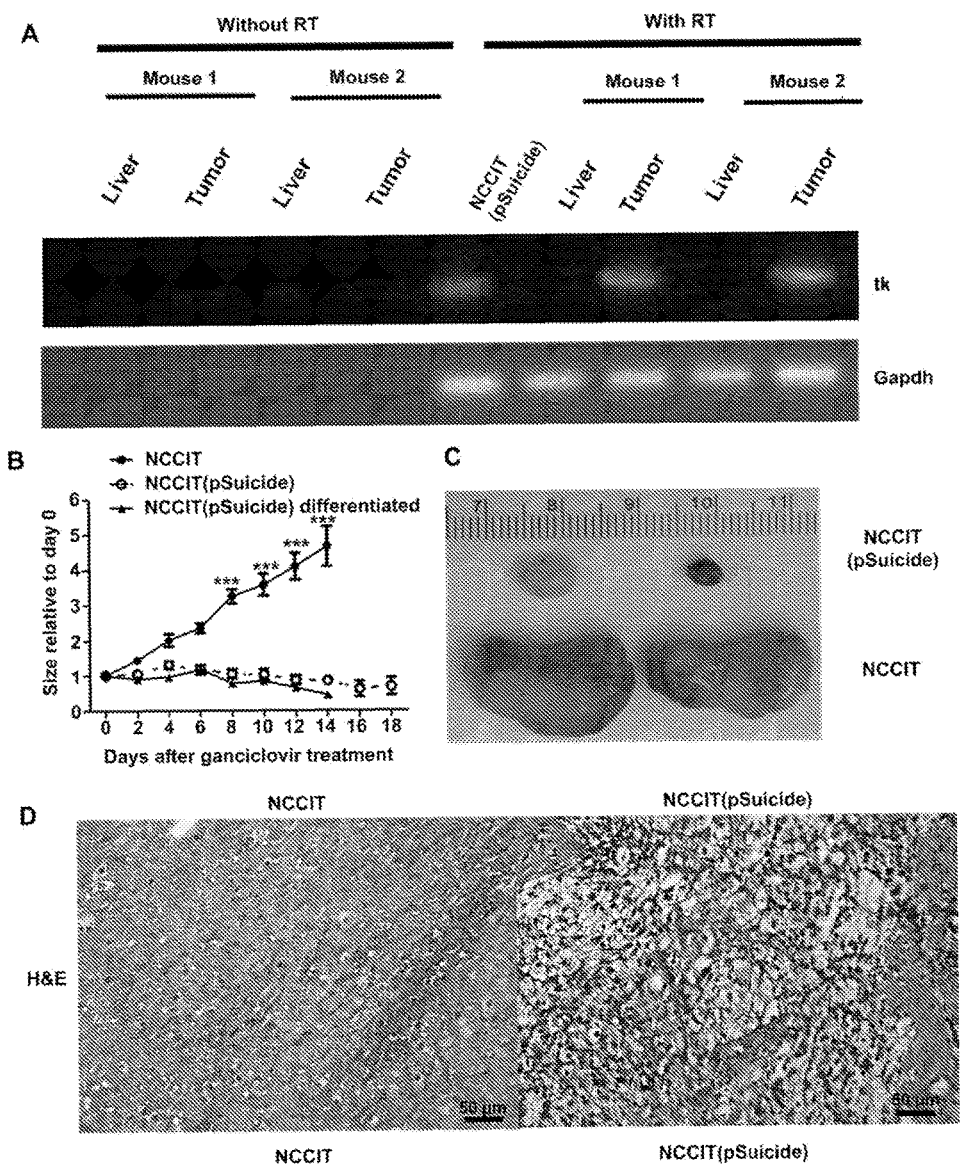

FIG. 5, comprising FIGS. 5A through 5D, depicts a graph and images showing safeguarding against tumor-forming pluripotent stem cells in vivo with pSuicide. FIG. 5A: Expression of tk mRNA in tumors but not normal liver tissues. Total RNA was isolated from tissues and tumors listed. cDNA from NCCIT (pSuicide) cells was used as a positive control. No products amplified from negative controls omitted reverse transcriptase (RT) during reverse transcription. Gapdh primers were designed to amply both human and mouse Gapdh cDNA. FIG. 5B: Ganciclovir inhibited growth of tumors from NCCIT (pSuicide) cells but not from NCCIT cells. Tumor size on the day ganciclovir was first delivered was set as 1. Means±SEM from 7 NCCIT-derived tumors (one mouse developed 3 separate tumors) and 4 NCCIT (pSuicide)-derived tumors are presented. Mice with NCCIT-derived tumors were sacrificed 2 weeks after ganciclovir administration due to the limitation on tumor size. *** Indicates p<0.0001 by Bonferroni post-tests following ANOVA. FIG. 5C: Sizes of tumors from NCCIT and NCCIT/Suicide cells after ganciclovir treatment. Scale unit: cm. FIG. 5D: Hematoxylin and eosin (H & E) staining of tumors formed by NCCIT and NCCIT (pSuicide) cells after ganciclovir treatment.

DETAILED DESCRIPTION

The present invention relates to compositions that enable the selective expression of a target gene in a subset of cells. In one embodiment, the compositions enable the elimination of undifferentiated stem cells from a cell population. Transplanted stem cells are an attractive option for potential therapies in a wide range of diseases and disorders due to their unique ability to differentiate into a variety of cell types. However, differentiation of stem cells is rarely 100% effective, and the residual undifferentiated stem cells have the potential to generate tumors.

In one embodiment, the present invention provides a construct comprising a first nucleic acid sequence comprising an episomal maintenance element and a second nucleic acid sequence comprising a target gene wherein the expression of the episomal maintenance element is regulated by a constitutive promoter and the expression of the target gene is regulated by a non-constitutive promoter. Preferably, the episomal maintenance element is the S/MAR element. An advantage of the present construct is that episomal maintenance element (e.g., the S/MAR element) and the target gene are controlled by two different promoters, for example, the promoter controlling the target gene can be non-constitutive without affecting the episomal maintenance of the construct.

In one embodiment, the construct of the invention does not integrate with the cell genome, therefore remaining in an episomal construct.

In one embodiment, the present invention provides a construct that enables the non-constitutive and/or inducible expression of a target gene. Preferably, the target gene of the present invention is a suicide gene. An exemplary suicide gene is thymidine kinase (TK). However, the invention should not be limited to TK. Rather, the invention is applicable to any suicide gene. In one embodiment, the expression of the target gene in a cell facilitates the death of the cell.

In one embodiment, the constructs of the present invention provides for the inducible expression of the target gene only in undifferentiated stem cells. Therefore, the inducible expression of the target gene in undifferentiated stem cells facilitates the selective death of undifferentiated stem cells. Preferably, the inducible expression of the target gene is driven by a promoter that is active only in stem cells. Preferably pluripotent stem cells.

In another embodiment, the constructs of the present invention provides for the inducible expression of the target gene in a specific cell type by way of operably linking the target gene with a promoter that is only active in a desired cell type. In this aspect, the expression of the target gene is inducible based on whether the promoter driving the target gene is active in the cell type. Therefore, the inducible expression of the target gene in a specific cell type facilitates the selective death of the desired cell type. That is, the inducible expression of the target gene is driven by a non-constitutive promoter including but is not limited to an inducible promoter, a cell-type specific promoter, a stem cell specific promoter, a tissue specific promoter, a tumor specific promoter.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Allogeneic" refers to a graft derived from a different animal of the same species.

As used herein, the term "autologous" is meant to refer to any material derived from the same individual.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced from or produced outside an organism, cell, tissue or system.

The term "expression" as used herein is defined as the transcription and/or translation of a particular nucleotide sequence driven by its promoter.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

"In vivo" gene delivery, gene transfer, gene therapy and the like as used herein, are terms referring to the introduction of a vector comprising an exogenous polynucleotide directly into the body of an organism, such as a human or non-human mammal, whereby the exogenous polynucleotide is introduced into a cell of such organism in vivo.

As used herein, an "instructional material" includes a publication, a recording, a diagram, or any other medium of expression which can be used to communicate the usefulness of a compound, composition, vector, or delivery system of the invention in the kit for effecting alleviation of the various diseases or disorders recited herein. Optionally, or alternately, the instructional material can describe one or more methods of alleviating the diseases or disorders in a cell or a tissue of a mammal. The instructional material of the kit of the invention can, for example, be affixed to a container which contains the identified compound, composition, vector, or delivery system of the invention or be shipped together with a container which contains the identified compound, composition, vector, or delivery system. Alternatively, the instructional material can be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

As used herein, "long term episomal maintenance" refers to the maintenance of the composition within a cell population over an extended period of time without the integration of the composition into the native genome of the cells.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" or "overexpression" is intended to indicate an abnormal level of expression of a gene or encoded protein in a first cell type relative to the level of expression the gene or encoded protein in a second cell type.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR™, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

The term "transfected" or "transformed" or "transduced" as used herein refers to a process by which exogenous nucleic acid is transferred or introduced into the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

A "therapeutic" treatment is a treatment administered to a subject who exhibits signs of pathology, for the purpose of diminishing or eliminating those signs.

As used herein, "treating a disease or disorder" means reducing the frequency with which a symptom of the disease or disorder is experienced by a patient. Disease and disorder are used interchangeably herein.

The phrase "therapeutically effective amount," as used herein, refers to an amount that is sufficient or effective to prevent or treat (delay or prevent the onset of, prevent the progression of, inhibit, decrease or reverse) a disease or condition, including alleviating symptoms of such diseases.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

"Xenogeneic" refers to a graft derived from an animal of a different species.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention relates to a strategy for the selective elimination of residual pluripotent stem cells from differentiated target cells to safeguard against unwanted proliferation of pluripotent stem cells in cell therapy.

The present invention relates to compositions and methods for the targeted elimination of a desired cell type, for example undifferentiated stem cells. While stem cell therapy remains an attractive option for numerous therapeutic strategies, the tumorigenicity of pluripotent stem cells hampers such strategies. The present invention provides for the selective elimination of undifferentiated stem cells, thus overcoming the tumorigenicity of transplanted stem cells. However, the invention should not be limited to only targeting stem cells for destruction. Rather, any cell type can be targeted for elimination using the constructs of the present invention. That is, the constructs of the present invention provides for the inducible expression of a target gene (e.g., suicide gene) in a specific cell type by way of operably linking the target gene with a promoter that is only active in a desired cell type.

In one embodiment, the present invention relates to a composition that has long term maintenance in a cell population while simultaneously providing the non-constitutive and/or inducible expression of a target gene in a subset of cells. In one embodiment, compositions of the invention are maintained in an episomal state, and are thus not incorporated into the cell genome. Compositions can include nucleotide sequences, plasmids, vectors, constructs, and the like, which encode for the expression of a target gene. In some instances, it is beneficial for exogenous compositions to not integrate into the genome as integration can cause mutagenesis. In one embodiment, long term episomal maintenance of the compositions of the invention is provided by the inclusion of the S/MAR element within the composition of the invention.

In one embodiment, the present invention provides compositions that induce the cell type specific expression of a target gene. In one embodiment, the expression of the target gene makes the cell susceptible to cell death. Thus, the present invention provides for the cell type specific induction of cell death, thereby eliminating a specific subset of cells from a cell population. Cell type specific expression of the target gene is controlled by an upstream cell type specific promoter. In one embodiment, the cell type specific promoter is specific to undifferentiated stem cells. An example of a cell type specific promoter that is only active in stem cells is the OCT4 promoter. However, the invention is not limited to only the OCT4 promoter. Rather, any promoter that is specifically active in stem cells and inactive in differentiated cells is included in the present invention.

In one embodiment, the compositions of the present invention provide long term maintenance of the episomal state in an entire cell population while also providing the cell type specific expression of a target gene. In one embodiment, the composition of the invention comprises two distinct promoter regions. In one embodiment, one promoter is a constitutive promoter upstream of an episomal maintenance region (e.g. S/MAR element), while the other promoter is a cell type specific promoter that drives the expression of the target gene.

The present invention also provides methods for the cell type specific expression of a target gene in a subset of cells. In one embodiment, the methods of the invention comprise providing a population of cells with a composition which enables the cell type specific expression of a target gene. In one embodiment, the composition also enables the long term episomal maintenance of the vector such that the vector is not integrated into the cell genome.

In one aspect, the present invention provides for methods of eliminating a specific subset of cells from a cell population by providing the entire population of cells with a composition that enables the cell type specific expression of a target gene that provides susceptibility to cell death. In one embodiment, the composition also enables the long term episomal maintenance of the vector such that the vector is not integrated into the cell genome.

Vectors

The present invention encompasses a DNA construct comprising sequences of at least one promoter sequence and a target gene. In one embodiment, the construct further comprises the sequence of an episomal maintenance element (e.g. S/MAR). Preferably, the S/MAR sequence and the target gene is controlled by different promoters. Therefore, the present invention provides a plasmid DNA construct that is able to maintain an episomal state no matter whether the target gene is expressed because the expression of the S/MAR is independent from the expression of the target gene.

In one embodiment, the S/MAR sequence is constitutive expressed while the target gene is controlled by a cell type specific promoter. An example of a cell type specific promoter is a promoter that is only active in stem cells and inactive in differentiated cells. Therefore, when the construct of the invention is present in a stem cell, the S/MAR sequence is expressed while the target gene is not expressed given that the cell type specific promoter (e.g., stem cell specific promoter) is not active in stem cells.

The nucleic acid sequences coding for the desired molecules can be obtained using recombinant methods known in the art, such as, for example by screening libraries from cells expressing the gene, by deriving the gene from a vector known to include the same, or by isolating directly from cells and tissues containing the same, using standard techniques. Alternatively, the gene of interest can be produced synthetically, rather than cloned.

In brief summary, the expression of natural or synthetic nucleic acids encoding polypeptides is typically achieved by operably linking a nucleic acid encoding the polypeptide or portions thereof to a promoter, and incorporating the construct into an expression vector. The vectors can be suitable for replication and integration eukaryotes. Typical cloning vectors contain transcription and translation terminators, initiation sequences, and promoters useful for regulation of the expression of the desired nucleic acid sequence.

The expression constructs of the present invention may also be used for nucleic acid immunization and gene therapy, using standard gene delivery protocols. Methods for gene delivery are known in the art. See. e.g., U.S. Pat. Nos. 5,399,346, 5,580,859, 5,589,466, incorporated by reference herein in their entireties. In another embodiment, the invention provides a gene therapy vector.

The nucleic acid can be cloned into a number of types of vectors. For example, the nucleic acid can be cloned into a vector including, but not limited to a plasmid, a phagemid, a phage derivative, an animal virus, and a cosmid. Vectors of particular interest include expression vectors, replication vectors, probe generation vectors, and sequencing vectors.

Further, the expression vector may be provided to a cell in the form of a viral vector. Viral vector technology is well known in the art and is described, for example, in Sambrook et al. (2001, Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpes viruses, and lentiviruses. In general, a suitable vector contains an origin of replication functional in at least one organism, a promoter sequence, convenient restriction endonuclease sites, and one or more selectable markers, (e.g., WO 01/96584; WO 01/29058; and U.S. Pat. No. 6,326,193).

A number of viral based systems have been developed for gene transfer into mammalian cells. For example, retroviruses provide a convenient platform for gene delivery systems. A selected gene can be inserted into a vector and packaged in retroviral particles using techniques known in the art. The recombinant virus can then be isolated and delivered to cells of the subject either in vivo or ex vivo. A number of retroviral systems are known in the art. In some embodiments, adenovirus vectors are used. A number of adenovirus vectors are known in the art. In one embodiment, lentivirus vectors are used.

Additional promoter elements, e.g., enhancers, regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the thymidine kinase (tk) promoter, the spacing between promoter elements can be increased to 50 bp apart before activity begins to decline. Depending on the promoter, it appears that individual elements can function either cooperatively or independently to activate transcription.

One example of a suitable promoter is the immediate early cytomegalovirus (CMV) promoter sequence. This promoter sequence is a strong constitutive promoter sequence capable of driving high levels of expression of any polynucleotide sequence operatively linked thereto. Another example of a suitable promoter is Elongation Growth Factor-1α (EF-1α). However, other constitutive promoter sequences may also be used, including, but not limited to the simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, as well as human gene promoters such as, but not limited to, the actin promoter, the myosin promoter, the hemoglobin promoter, and the creatine kinase promoter. Further, the invention should not be limited to the use of constitutive promoters. Inducible promoters are also contemplated as part of the invention. The use of an inducible promoter provides a molecular switch capable of turning on expression of the polynucleotide sequence which it is operatively linked when such expression is desired, or turning off the expression when expression is not desired. Examples of inducible promoters include, but are not limited to a metallothionine promoter, a glucocorticoid promoter, a progesterone promoter, and a tetracycline promoter.

In order to assess the expression of a polypeptide or portions thereof, the expression vector to be introduced into a cell can also contain either a selectable marker gene or a reporter gene or both to facilitate identification and selection of expressing cells from the population of cells sought to be transfected or infected through viral vectors. In other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes, such as neo and the like.

Reporter genes are used for identifying potentially transfected cells and for evaluating the functionality of regulatory sequences. In general, a reporter gene is a gene that is not present in or expressed by the recipient organism or tissue and that encodes a polypeptide whose expression is manifested by some easily detectable property, e.g., enzymatic activity. Expression of the reporter gene is assayed at a suitable time after the DNA has been introduced into the recipient cells. Suitable reporter genes may include genes encoding luciferase, beta-galactosidase, chloramphenicol acetyl transferase, secreted alkaline phosphatase, or the green fluorescent protein gene (e.g., Ui-Tei et al., 2000 FEBS Letters 479: 79-82). Suitable expression systems are well known and may be prepared using known techniques or obtained commercially. In general, the construct with the minimal 5' flanking region showing the highest level of expression of reporter gene is identified as the promoter. Such promoter regions may be linked to a reporter gene and used to evaluate agents for the ability to modulate promoter-driven transcription.

Methods of introducing and expressing genes into a cell are known in the art. In the context of an expression vector, the vector can be readily introduced into a host cell, e.g., mammalian, bacterial, yeast, or insect cell by any method in the art. For example, the expression vector can be transferred into a host cell by physical, chemical, or biological means.

Physical methods for introducing a polynucleotide into a host cell include calcium phosphate precipitation, lipofection, particle bombardment, microinjection, electroporation, and the like. Methods for producing cells comprising vectors and/or exogenous nucleic acids are well-known in the art. See, for example, Sambrook et al. (2001, Molecular Cloning: A Laboratory Manual, Cold Spring Harbor Laboratory, New York). A preferred method for the introduction of a polynucleotide into a host cell is calcium phosphate transfection.

Biological methods for introducing a polynucleotide of interest into a host cell include the use of DNA and RNA vectors. Viral vectors, and especially retroviral vectors, have become the most widely used method for inserting genes into mammalian, e.g., human cells. Other viral vectors can be derived from lentivirus, poxviruses, herpes simplex virus I, adenoviruses and adeno-associated viruses, and the like. See, for example, U.S. Pat. Nos. 5,350,674 and 5,585,362.

Chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle).

In the case where a non-viral delivery system is utilized, an exemplary delivery vehicle is a liposome. The use of lipid formulations is contemplated for the introduction of the nucleic acids into a host cell (in vitro, ex vivo or in vivo). In another aspect, the nucleic acid may be associated with a lipid. The nucleic acid associated with a lipid may be encapsulated in the aqueous interior of a liposome, interspersed within the lipid bilayer of a liposome, attached to a liposome via a linking molecule that is associated with both the liposome and the oligonucleotide, entrapped in a liposome, complexed with a liposome, dispersed in a solution containing a lipid, mixed with a lipid, combined with a lipid, contained as a suspension in a lipid, contained or complexed with a micelle, or otherwise associated with a lipid. Lipid, lipid/DNA or lipid/expression vector associated compositions are not limited to any particular structure in solution. For example, they may be present in a bilayer structure, as micelles, or with a "collapsed" structure. They may also simply be interspersed in a solution, possibly forming aggregates that are not uniform in size or shape. Lipids are fatty substances which may be naturally occurring or synthetic lipids. For example, lipids include the fatty droplets that naturally occur in the cytoplasm as well as the class of compounds which contain long-chain aliphatic hydrocarbons and their derivatives, such as fatty acids, alcohols, amines, amino alcohols, and aldehydes.

Lipids suitable for use can be obtained from commercial sources. For example, dimyristyl phosphatidylcholine ("DMPC") can be obtained from Sigma, St. Louis, Mo.; dicetyl phosphate ("DCP") can be obtained from K & K Laboratories (Plainview, N.Y.); cholesterol ("Choi") can be obtained from Calbiochem-Behring; dimyristyl phosphatidylglycerol ("DMPG") and other lipids may be obtained from Avanti Polar Lipids, Inc. (Birmingham, Ala.). Stock solutions of lipids in chloroform or chloroform\methanol can be stored at about −20° C. Chloroform is used as the only solvent since it is more readily evaporated than methanol. "Liposome" is a generic term encompassing a variety of single and multilamellar lipid vehicles formed by the generation of enclosed lipid bilayers or aggregates. Liposomes can be characterized as having vesicular structures with a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh et al., 1991 Glycobiology 5: 505-10). However, compositions that have different structures in solution than the normal vesicular structure are also encompassed. For example, the lipids may assume a micellar structure or merely exist as nonuniform aggregates of lipid molecules. Also contemplated are lipofectamine-nucleic acid complexes.

Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention.

Compositions

The present invention relates to compositions that provide long term maintenance of the episomal state of the composition. In one embodiment, the composition of the invention does not integrate into the cell genome. In some instances, it is beneficial for exogenously applied nucleotide sequences to remain in an episomal state, i.e. not become integrated into the native genome.

The compositions of the present invention comprise an episomal maintenance element that aids in the long term episomal maintenance of the composition. As used herein, "long term episomal maintenance" refers to the maintenance of the composition within a cell population over an extended period of time without the integration of the composition into the native genome of the cells. In one embodiment, long term episomal maintenance is achieved through the replication and segregation of the composition into daughter cells during cell division.

In one embodiment, the episomal maintenance element is the S/MAR region. Transcription of the S/MAR region stably maintains the composition in an episomal state. The composition (e.g. vector or construct) replicates once per cell cycle during early S-phase, with the origin recognition complex assembled at various regions on the vector DNA (Schaarschmidt et al., 2004, Embo J, 23: 191-201). Origin recognition complex stably interacts with metaphase chromosomes, which leads to stable episomal maintenance (Baiker et al., 2000, Nat Cell Biol, 2: 182-184). S/MAR based vectors do not integrate into the genome of mammalian cells and mediate long term gene transfer, they have reduced risk of insertional mutagenesis. Also, they would be less immunogenic than viral vectors since they have fewer non-human sequences. However, the present invention is not limited to the inclusion of S/MAR as the episomal maintenance element of the composition. Rather, the episomal maintenance element can be any region known in the art to induce the long term episomal maintenance of the composition. For example, in one embodiment the composition can comprise the oriP and EBNA-1 sequences, wherein the oriP/EBNA-1 system induces the replication of the construct once per cell cycle.

In one embodiment of the compositions of the invention, the episomal maintenance element is downstream of a promoter element which regulates the transcription of the episomal maintenance element. The promoter element may be represented by any suitable promoter inserted upstream of the episomal maintenance element, and can include constitutive, cell-cycle specific, tissue specific, metabolically regulated, or inducible promoters or "enhancers". In a preferred embodiment, the promoter sequence that drives transcription of the episomal maintenance element is a constitutive promoter such that transcription occurs at all times in all cells. Non-limiting examples of constitutive promoters that can be included in the construct of the invention include, but are not limited to the CMV promoter, elongation factor-1 (EF1) promoter, simian virus 40 (SV40) early promoter, mouse mammary tumor virus (MMTV), human immunodeficiency virus (HIV) long terminal repeat (LTR) promoter, MoMuLV promoter, an avian leukemia virus promoter, an Epstein-Barr virus immediate early promoter, a Rous sarcoma virus promoter, the actin promoter, the myosin promoter, the hemoglobin promoter, and the creatine kinase promoter, the GAPDH promoter, the Ubiquitin B promoter, the FerH promoter, the FerL promoter, and the like.

The present invention relates to compositions that provide non-constitutive expression of a target gene (e.g., suicide gene). In some instances it is preferable to only express the target gene in a subset of cells. This subset of cells can differ from a larger cell population by difference in cell type, age, metabolic activity, cell-cycle, and the like. Non-constitutive expression of a target gene can be implemented by placing the sequence encoding the target gene under the control of a non-constitutive promoter. Such promoters can be cell-cycle specific, tissue specific, metabolically regulated, or inducible promoters or "enhancers". By inclusion of such non-constitutive promoters, expression of the target gene is thereby regulated to occur only under defined conditions. As would be understood by those skilled in the art, the target gene of the present composition can be any gene known in the art. That is, the present invention is not limited to the type of gene encoded by the composition.

The present invention relates to a composition that provides long term episomal maintenance in an entire cell population while providing non-constitutive expression of a target gene in a subset of cells. In current S/MAR based episomal compositions, the S/MAR sequence is transcribed by the same promoter that drives the transcription of a target gene. Thus, episomal maintenance, in these compositions, occurs only in cells in which the target gene is expressed. The present invention is based upon the discovery that a composition where the S/MAR region is driven by a constitutive promoter, while the target gene is driven by a separate non-constitutive promoter can induce the long term episomal maintenance in a whole cell population while inducing the expression of the target gene in a subset of cells. This allows the composition to exist long term in a cell population and provide selective expression of a target gene if a cell from the cell population is altered to state in which expression is desired. Thus, in one embodiment, the present invention comprises an episomal maintenance element (e.g. S/MAR) driven by a constitutive promoter, and a target gene driven by a non-constitutive promoter. In one embodiment, the compositions of the invention induce the expression of the target gene in undifferentiated pluripotent stem cells. The present construct induces the selective expression of the target gene by the identity of the promoter element that drives the target gene. For example, for the selective expression of the target gene in undifferentiated pluripotent stem cells, the construct can comprise the target gene downstream of a promoter element that is specific for undifferentiated pluripotent stem cells. Non-limiting examples of promoter elements that are specific for undifferentiated pluripotent stem cells include OCT4, hTERT, and NANOG. The long term episomal maintenance of the compositions in an entire cell population enables the expression of a target gene in a cell that may de-differentiate into an undifferentiated pluripotent stem cell. However, the present invention is not limited to selective expression of the target gene in undifferentiated pluripotent stem cells. Rather, the non-constitutive promoter element can be of any type known in the art that provides a selective expression of the target gene in a specific cell type. For example, the non-constitutive promoter can be a cell-specific promoter including but not limited to, B29 promoter (B cells), CD45 promoter (hematopoietic stem cells), desmin promoter (muscle), GFAP promoter (astrocytes), SYNI promoter (neurons), and the like. In another embodiment, the non-constitutive promoter can be a tumor specific promoter including, but not limited to, CCKAR promoter (pancreatic cancer), CEA (epithelial cancer), PSA (prostate cancer), HE4 promoter, E2F-1 promoter, and the like. In yet another embodiment, the non-constitutive promoter can be an inducible promoter, which allows the expression of the target gene to be regulated by the presence or absence of some biological or non-biological factor. Examples of inducible promoters include, but are not limited to, metallothionine promoter, a glucocorticoid promoter, a progesterone promoter, tetracycline promoter, HSP70 promoter (heat), GRP94 promoter (stress), EGR1 promoter (radiation), and the like.

The present invention is based upon the selective elimination of a subset of cells from a cell population. In one embodiment, the compositions of the invention induce the non-constitutive expression of a target gene in a subset of cells that makes that subset of cells susceptible for cell death. For example, in one embodiment, the composition provides for the selective expression of a death inducing target gene in undifferentiated pluripotent stem cells, thereby making the undifferentiated pluripotent stem cells, which may exist within a larger population of predominately differentiated cells, susceptible for cell death. Susceptibility for cell death in conferred to the subset of cells through the identity of the target gene. For example in one embodiment, the target gene encodes for the expression of thymidine kinase (TK). TK converts non-toxic ganciclovir into toxic ganciclovir triphosphate. Thus, cells that selectively express TK will die upon exposure to ganciclovir, while cells that do not express TK will survive. However, the present invention is not limited to constructs that encode TK. Other, non-limiting examples of proteins which can induce the susceptibility of cell death and that can be encoded on the present construct, include cytosine deaminase which converts non-toxic 5-fluorocytosine into toxic 5-fluorouracil, Caspase-9, and α-1,3-galactosyltransferase which synthesizes a sugar chain absent in humans thus causing an immune response.

In one embodiment, the compositions of the present invention comprise a nucleotide sequence that corresponds to the S/MAR element and a nucleotide sequence that encodes TK. As described elsewhere herein, the compositions enable the constitutive expression of S/MAR and the non-constitutive or inducible expression of TK. Thus, in one embodiment, the composition comprises the EF1 promoter region that drives the constitutive expression of S/MAR and the OCT4 promoter region that drives the selective expression of TK in undifferentiated pluripotent stem cells.

Methods

The present invention is related to methods of inducing the selective expression of a target gene in a subset of cells. In one embodiment, the method comprises the administration to a cell population of a composition that includes the nucleotide sequence that encodes for the target gene under the control of a non-constitutive or inducible promoter. Thus, the expression of the target gene occurs only in cells in which the non-constitutive or inducible promoter is active. For example, the composition can comprise an OCT4 promoter, which is active only in undifferentiated pluripotent stem cells, thereby inducing the expression of the target gene only in undifferentiated pluripotent stem cells.

As described elsewhere herein, the compositions of the invention also comprise an episomal maintenance element (e.g. S/MAR) under the control of a constitutive promoter. Thus, in the methods of the present invention, the administered compositions have long term episomal maintenance in an entire cell population while inducing the selective expression of a target gene in a subset of cells. Therefore, in one embodiment the methods of the invention relate to the selective expression of a target gene in a cell of a cell population when the cell is altered to a cellular state in which expression of the target gene is desired. For example, the method can comprise administering a composition to an entire cell population, wherein all cells in the cell population are in a state that does not induce the expression of the gene. In one embodiment, when a cell from the population is altered to a second state, where that cell is now different from the population in cell type, metabolic activity, cell-cycle, etc., the composition induces the selective expression of the target gene. In another embodiment, the method can comprise administering the composition to a population of cells, wherein all the cells are in a state that induces the expression of a target gene. In one embodiment, when a cell from the cell population is altered to a second state, where the cell is now different from the population in cell type, metabolic activity, cell-cycle, etc., the expression of the target gene is suppressed. Thus, the methods of the present invention relate to the regulation of the expression of a target gene in a cell, dependent on the changing state of the cell.

The present method is not limited to the type of change that occurs in the cell. For example, the cell can differentiate, de-differentiate, become cancerous, etc. The change is only limited in that the activity of the non-constitutive or inducible promoter that drives the expression of the target gene is altered by the change in state of the cell. The long term episomal maintenance of the composition provides the ability for a cell to regulate the expression of the target gene well after the initial application of the composition. This prevents the need for frequent or continual application of the composition to the cell population.

The present invention relates to methods of eliminating undifferentiated pluripotent stem cells from a cell population. Pluripotent human embryonic stem cells and induced pluripotent stem (iPS) cells provide limitless cell sources for tissue regeneration (Thomson et al., 1998, Science, 282: 1145-1147; Takahashi et al., 2006, Cell, 126: 663-676; Okita et al., 2007, Nature, 448: 313-317 ; Yu et al., 2007, Science, 318: 1917-1920). Embryonic stem cells and iPS cells both have the risk of forming tumors and this issue needs to be addressed before they find application in clinic. While in most cases embryonic stem cells and iPS cells will be differentiated into target cells before they are transplanted to patients, the risk of tumor formation is still significant since no differentiation protocol can be 100% efficient and there will be residual pluripotent stem cells even after selection based on cell surface markers.

The present invention provides methods to eliminate the residual pluripotent stem cells thereby preventing tumorigenicity of stem cell therapies. In one embodiment, the method comprises the administration to a cell population of a composition that includes the nucleotide sequence that encodes for the target gene under the control of an undifferentiated pluripotent stem cell specific promoter. For example, the undifferentiated pluripotent stem cell specific promoter can be OCT4, hTERT, NANOG, and the like.

In one embodiment, the target gene encodes a polypeptide that makes the undifferentiated pluripotent stem cell susceptible for cell death. For example, as described elsewhere herein, the target gene can encode for the expression of thymidine kinase (TK), cytosine deaminase, Caspase-9, α-1,3-galactosyltransferase and the like. In one embodiment, wherein the composition induces the selective expression of TK, the method further comprises administering an effective amount of ganciclovir to the cell population. Cells expressing TK convert the non-toxic ganciclovir to toxic ganciclovir triphosphate, which therefore causes the cell death of the TK expressing cells. In one embodiment, by driving TK expression off of an undifferentiated pluripotent stem cell specific promoter (e.g. OCT4), the method provides the selective elimination of undifferentiated pluripotent stem cells from the cell population.

In one embodiment, the applied composition of the method comprises an episomal maintenance element (e.g. S/MAR) driven off of a constitutive promoter. Thus, the applied composition has long term episomal maintenance in the entire cell population. This ensures that any cell that de-differentiates into an undifferentiated pluripotent stem cell at some time after the original application of the composition will still carry the composition and therefore selectively express the target gene (e.g., TK) to induce its death.

As would be understood by those skilled in the art, the methods of eliminating undifferentiated pluripotent stem cells can be carried out in vitro, ex vivo, in vivo, or a combination thereof. For example, in one embodiment, the method comprises the in vitro administration of a composition that provides selective expression of TK in undifferentiated stem cells to a cell population, and an in vitro administration of ganciclovir to the cell population to cause the cell death of the TK expressing cells. In another embodiment, the method comprise the in vitro administration to a cell population of a composition of the invention that provides selective expression of TK in undifferentiated cells to a cell population, the transplantation of the cell population into a subject, and the in vivo administration of ganciclovir to the subject to cause the cell death of the TK expressing cells.

In one embodiment, the present invention comprises genetically modifying a population of stem cells. Differentiation of stem cells is rarely 100% efficient and residual undifferentiated stem cells are tumorigenic. In one embodiment, the present method relates to genetically modifying a population of stem cells to selectively express a target gene in undifferentiated stem cells. In one embodiment, selective expression of the target gene in undifferentiated stem cells results in increased susceptibility for cell death in the undifferentiated stem cells. In one embodiment, the method comprises administering the composition comprising the target gene driven off an undifferentiated stem cell specific promoter (e.g. OCT4) to a population of primarily undifferentiated stem cells.

In another embodiment, the method comprises administering the composition comprising the target gene driven off an undifferentiated stem cell specific promoter (e.g. OCT4) to a population of stem cells that have been induced to differentiate. In one embodiment, the methods of genetically modifying a population of cells comprises administering a composition that further comprises an episomal maintenance element (e.g. S/MAR) driven off of a constitutive promoter. In this aspect, the episomal maintenance element provides long term episomal maintenance of the applied composition in the genetically modified cells. As would be understood by those skilled in the art, the method of genetically modifying the cells can occur in an in vitro, ex vivo, or in vivo environment.

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Safeguarding Pluripotent Stem Cells for Cell Therapy with a Non-Viral, Non-Integrating Episomal Suicide Construct Pluripotent stem cells provide an unlimited cell source for cell therapy. However, residual pluripotent stem cells after differentiation can form tumors. Modifying stem cells with suicide constructs through integrating plasmid DNA and viral vectors has previously been attempted to specifically eliminate residual pluripotent stem cells after differentiation. However, in such cases, integration of foreign DNA has the potential of insertional mutagenesis, position effects and silencing. Scaffold/matrix attachment region (S/MAR)-based plasmid DNA can be maintained extra-chromosomally, offering a safer alternative to integrating vectors for this purpose. Accordingly, the design of an S/MAR-based suicide construct capable of episomal maintenance and specifically killing pluripotent stem cells but not differentiated cells in the presence of ganciclovir is disclosed herein. The episomal suicide construct of the present invention has been designed such that the thymidine kinase (tk) gene is only expressed in pluripotent stem cells, yet is able to maintain the episomal state independent of the expression of the target gene. Treating cells differentiated from episomal suicide construct-modified stem cells with ganciclovir reduces the tumor formation risk after cell transplantation. Tumors formed by such modified pluripotent stem cells could be inhibited by ganciclovir administration. The episomal suicide construct of the present invention enables negative selection of residual pluripotent stem cells in vitro and control of tumors formed from residual pluripotent stem cells in vivo.

This experimental example relates to the design of a new S/MAR-based episomal plasmid with constitutive transcription of the S/MAR sequence for episomal maintenance, and a second expression cassette for controllable gene expression. The new episomal plasmid is able to maintain a stable and high level of expression of target genes. An S/MAR-based episomal suicide construct containing the pluripotent stem cell-specific OCT4 promoter and HSV tk suicide gene confers ganciclovir sensitivity to pluripotent stem cells. In vitro ganciclovir selection of episomal suicide construct-modified cells before transplantation reduced the risk of tumor formation. In addition, in vivo ganciclovir administration inhibited the growth of tumors from suicide construct-modified cells. The data demonstrates that it is possible to safeguard pluripotent stem cells for cell therapy with a non-viral, non-integrating episomal suicide construct.

The materials and methods employed in these experiments are now described.

Materials and Methods

Plasmids pEPI-eGFP was a kind gift from Dr. Hans-Joachim Lipps (Universität Witten/Herdecke). pS/MAR-GFP1 and pS/MAR-GFP2 were constructed based on the backbone of pEGFP-C2 (BD Biosciences, Franklin Lakes, N.J.). pEGFP-C2 was cut with AseI and BglII to delete the CMV promoter and EGFP coding sequences to obtain plasmid pEGFP-C2Δ. Then the SexAI-StuI fragment of pEGFP-C2Δ (containing the SV40 origin of replication and SV40 early promoter sequences) was replaced by a SexAI-SmaI fragment of the human EF1α promoter sequence amplified from pWPXL (Addgene, Cambridge, Mass.) with the primers EF1-F (GAG ACC AGG TCG TGA GGC TCC GGT GCC CGT CAG TGG: SEQ ID NO: 1) and EF1-R (ATA CCC GGG CAC GAC ACC TGA AAT GGA AGA AA; SEQ ID NO: 2), resulting in the plasmid pEGFP-C2Δ/EF1. The 2 kb S/MAR sequence (Mielke et al., 1990, Biochemistry 29:7475-85) was amplified from pEPI-eGFP by the primers S/MAR-F (actccgggagATCTAAATAAACTTATAAATTGTGAG; SEQ ID NO: 3) and S/MAR-R (actccgggaGAATTCTAT-CAAATATTTAAAGAAAAAAAAATTG; SEQ ID NO: 4) and inserted into the PfoI site of pEGFP-C2Δ/EF1 (downstream of the neomycin-resistance gene and upstream of polyadenylation signals), making the plasmid pS/MAR. The ApaLI-MscI fragment from pS/MAR was replaced by the ApaLI-MscI fragment of pEGFP-C2 (consisting of a CMV promoter and EGFP cDNA) to make plasmid pS/MAR-GFP1. Finally, a SalI-SmaI fragment from pWPXL containing the EF1α promoter and EGFP coding sequences was inserted between the SalI/SmaI sites of pS/MAR to obtain pS/MAR-GFP2. pSuicide was constructed by one-step ligation of the following three fragments: the KpnI-digested pS/MAR, the KpnI/BglII-digested human OCT4 promoter sequences from pOCT4-luc (Takahashi et al., 2006, Cell 126:663-76), and the KpnI/BglII-digested herpes simplex virus thymidine kinase (tk) cDNA amplified from pLG1 (a kind gift from Dr. Gan Lin at University of Rochester) by the primers TK-F1 (ACAAGATCTACCATGGCTTCGTAC-CCTGCCATC; SEQ ID NO: 5) and TK-R1 (ACGGTAC-CTCAGTTAGCCTCCCCCATCTCC; SEQ ID NO: 6).

Cell Culture and Transfection

CHO-K1 cells were cultivated in F-12 Nutrient Mixture medium containing 10% FBS. HeLa and NCCIT cells were cultivated in DMEM supplemented with 10% FBS and 1% glutamine. For cell transfection, $5 \times 10^4$ cells were seeded into one well of a 12-well plate, and overnight transfections were performed using 0.5 μg vector DNA and 2 μl Fugene 6 (Roche Applied Science, Germany) transfection reagent per well, following the manufacturer's instructions. To obtain clones, transfected cells were selected with medium containing 500 μg/ml G418 (Sigma-Aldrich, St. Louis, Mo.) for 2-3 weeks before colonies were picked. Individual clones were checked for episomal DNA by Southern blotting, as described herein.

Flow Cytometry Analysis of GFP Expression

Cells were trypsinized, fixed in 2% paraformaldehyde for 10 min at room temperature and washed with PBS buffer. GFP expression was analyzed using a BD FACSCalibur cytometer (BD Biosciences, San Jose, Calif.) with CellQuest software.

1. Flow Cytometry Analysis of GFP Expression

Cells were trypsinized, fixed in 2% paraformaldehyde for 10 min at room temperature and washed with PBS buffer. GFP expression was analyzed using a BD FACSCalibur cytometer (BD Biosciences, San Jose, Calif.) with CellQuest software.

2. Detection of Episomal DNA in Cells by Southern Blotting

Extra-chromosomal DNA was isolated from stable transfected CHO and NCCIT cells using a modified HIRT procedure (Hirt, 1967, J Mol Biol 26:365-9). Briefly, after removing the medium, cells on a 100-mm dish were directly washed in D-PBS, then lysed by adding 1 ml of Hirt buffer (10 mmol/L EDTA, pH 7.5 and 0.6% SDS). After incubating at room temperature for 20 min, the viscous lysate was transferred into an Eppendorf tube. A 5 mol/L of NaCl was used to create a final concentration of 1 mol/L NaCl in the lysed cells, and the sample was mixed gently. The lysate was incubated at 4° C. for more than 8 h, and centrifuged at 17,000 g for 30 min at 4° C. The supernatant was extracted with 25:24:1 phenol:chloroform:isoamyl alcohol. DNA was precipitated by adding an equal volume of isopropanol and washed with 70% ethanol. The pellet of DNA was dissolved in TE buffer by incubating for 1 h at 65° C.

Southern blotting was carried out with the DIG-High Prime DNA Labeling and Detection Starter Kit II (Roche Applied Science, Germany) according to the manufacturer's recommendations. pEGFP-C2, from which pSMAR-GFP2 and pSuicide were derived, was used as the template for probe preparation. One μg plasmid DNA was labeled with Digoxigenin-11-dUTP using DIG-High prime by incubating for up to 20 h at 37° C. The yield of DIG-labeled DNA was determined by comparing a series of dilutions of DIG-labeled DNA to the DIG-labeled control DNA.

Extra-chromosomal DNA isolated from two 100-mm dish cells was digested with BamHI (for pSMAR-GFP2) or EcoRV (for pSuicide) before being loaded on a 0.8% agarose gel. DNA gel electrophoresis, transfer, and fixation were performed according to standard Southern blotting protocols. Hybridization was carried out at 50° C. overnight in 5 ml hybridization solution containing 25 ng/ml DIG-labeled probe DNA. After post-hybridization washes, anti-Digoxigenin-AP immunological detection was performed and the hybridization signal was acquired by exposure to an LAS-3000 imager (Fujifilm Co., Japan) for 2-5 min at room temperature.

Cell Survival Under Ganciclovir Treatment

NCCIT and HeLa cells with and without pSuicide episomal DNA were treated with and without 2 μmol/L ganciclovir. Cell numbers and morphology were compared 7 days after treatment.

NCCIT Cell Differentiation and Elimination of Remaining OCT4-Expressing NCCIT Cells NCCIT cells were directly cultivated in standard DMEM medium containing 20 μmol/L retinoic acid to induce differentiation. NCCIT (pSuicide) cells were similarly cultured but included 400 μg/ml G418 in the differentiation medium. The differentiation medium was changed every other day. About 10 days after differentiation, the cells were split, counted, and divided into two aliquots. One aliquot of cells was maintained in differentiation medium containing 2 μmol/L ganciclovir for 7 days (for in vitro immuno-analysis) or 14 days (for in vivo tumor formation). As a negative control, counterpart cells were grown in differentiation medium containing 0.1% DMSO in which ganciclovir is dissolved.

Western Blotting Assay of OCT4 and Thymidine Kinase Expression

Cells were lysed in RIPA buffer with protease inhibitors (0.5 mmol/L PMSF and 1×Complete Protease Inhibitor Cocktail from Roche) for SDS-PAGE and Western blotting analyses. Monoclonal anti-β-actin antibody was from Sigma and used at 1:5000 (St Louis, Mo.). Rabbit anti-HSV thymidine kinase antiserum was obtained from Dr. William Summers of Yale University (1:5000); anti-OCT4A antibody was from Santa Cruz Biotechnology (Santa Cruz, Calif.) and used at 1:1000. Horseradish peroxidase (HRP)-conjugated secondary antibodies (1:1000) were purchased from Pierce (Rockford, Ill.). Chemiluminescent reagents from Pierce were used to visualize the protein signals on an LAS-3000 imaging system (Fujifilm). The Integrated Density function (Image J software) was used to quantify the expression of individual proteins after normalized by β-actin.

Immunofluorescent Analysis of Differentiated NCCIT Cells

OCT4 immunofluorescent staining was performed as described previously (Zhao et al., 2010, Stem Cells 28:229-39). Briefly, differentiated NCCIT cells growing on chamber slides were fixed in 4% PFA for 15 min at room temperature and permeabilized in 0.2% Triton X-100/PBS for 10 min. After blocking with 10% horse serum, cells were incubated with 3%0/horse serum diluted (1:50) OCT4 antibody (Santa Cruz Biotechnology) for 1 h at room temperature, followed by three washes in PBS-T (0.1% Tween 20 in phosphate-buffered saline). Cells were incubated with 1:200 diluted Texas Red-conjugated anti-mouse secondary antibody for 1 h at room temperature, and then washed again 3 times in PBS-T. Nuclei were counterstained with 4,6-diamidino-2-phenylindole (Sigma-Aldrich). Images were captured under a fluorescent microscope.

Flow Cytometry Analysis of OCT4-Expressing Cells

Cells were trypsinized and about $5 \times 10^5$ cells were fixed in 2% paraformaldehyde for 10 min at room temperature. Cells were pelleted and permeabilized by resuspension with vigorous vortexing in 500 μl iced-cold methanol and incubated at 4° C. for at least 10 min. After 3 washes with staining buffer (PBS with 1% BSA), the cells were resuspended in 100 μl OCT4 antibody (Santa Cruz Biotechnology), diluted to 1:100 with staining buffer, and incubated for 30 min at 4° C. The cells were washed 3 times with staining buffer and incubated in 1:300 diluted Cy5-conjugated goat anti-mouse Fab for 30 min at 4° C. The cells were assessed for OCT4 expression using a BD FACSCalibur cytometer (BD Biosciences) with CellQuest software.

In Vivo Tumor Formation and Ganciclovir Treatment

Trypsinized cells washed in PBS were resuspended in ice-cold PBS containing 30% BD Matrigel (BD Biosciences), drawn into an ice-cold 1-mL syringe, and kept on ice for subcutaneous injection into 8-~12-week-old female immunodeficient SCID mice (Charles River Laboratories, Wilmington, Mass.) as previously described (Prokhorova et al., 2009, Stem Cells Dev 2009; 18:47-54). For undifferentiated NCCIT and NCCIT (pSuicide) cells, $1.5 \times 10^6$ cells in 100 μl volume were injected for each mouse. For differentiated NCCIT (pSuicide) cells, $3 \times 10^6$ cells were injected.

Animals were housed in the animal facility of Wake Forest University Health Sciences. Experiments were conducted in accordance with the National Research Council publication *Guide for Care and Use of Laboratory Animals*, and approved by the Institutional Animal Care and Use Committee of Wake Forest University Health Sciences.

When tumors reached about 8 mm in size, ganciclovir (50 mg/kg body weight) was delivered intraperitoneally daily for 2-3 weeks. Each tumor was regarded as a prolate spheroid and the greatest longitudinal diameter (L) and greatest transverse diameter (B) were monitored with a caliper every 2 days by the same person. The two dimensions were to lie perpendicular to each other in a plane tangential to the body wall. Tumor size was estimated from the formula $V = \frac{1}{2}(L \times B^2)$ as previously described (Euhus et al., 1986, J Surg Oncol 31:229-34). The size of tumors formed by NCCIT and NCCIT (pSuicide) cells was compared by analysis of variation (ANOVA), setting as 1 the volume on the day ganciclovir was first delivered. Animal numbers injected for each cell type are listed in Table 1 and Table 2.

TABLE 1

Tumor development from RA-differentiated NCCIT(pSuicide) cells.[a]

| Cell type | Cells/mouse | Mice injected | No. mice with tumor | | | p Value (Fisher's exact test)[b] |
|---|---|---|---|---|---|---|
| | | | 0-3 Months postinjection | 3-5 Months postinjection | Total | |
| RA + GANC | $3 \times 10^6$ | 14 | 1 | 0 | 1 | 0.0158 |
| RA | $3 \times 10^6$ | 9 | 6 | 1 | 7 | |

[a] Due to the short lifespan of the SCID mice used, some mice died 4 months after cell injection without tumor. In addition, two mice injected with ganciclovir-selected cells died 2 months after cell injection without tumor, which were excluded from the statistical analysis.

[b] Only tumors formed 0-3 months after cell injection were included in the statistical analysis, since some mice died 4 months after injection.

TABLE 2

Tumor development from NCCIT(pSuicide) and NCCIT cells.[c]

| Cell | Cells/mouse | Mice injected | Mice with tumor 6 w postinjection | No. of tumors developed | Tumors responded to ganciclovir |
|---|---|---|---|---|---|
| NNCIT(pSuicide) | $1.5 \times 10^6$ | 6 | 4 | 4 | 4/4 |
| NCCIT | $1.5 \times 10^6$ | 6 | 5 | 7[d] | 0/7 |

[c]Fisher's exact test revealed no difference in rate of mice with tumors (P > 0.05).
[d]One mouse developed three tumors.

Cell and Tumor Nucleic Acid Analysis

Total DNA and RNA from tumor and normal tissues were extracted with DNeasy Blood & Tissue Kit and RNeasy Mini Kit (Qiagen), respectively. RNA was treated with DNase I (Ambion, Grand Island, N.Y.) to remove possible contaminating DNA. Reverse transcription was performed with the SuperScript™ First-Strand Synthesis System from Invitrogen. Equal amount of total DNA or cDNA was used as the template for polymerase chain reaction (PCR). GAPDH-F (5'-TGAAGGTCGGAGTCAACGGAT-3'; SEQ ID NO: 7) and GAPDH-R (5'-CCTGGAAGATGGT-GATGGGAT-3'; SEQ ID NO: 8), HSV tk-F (5'-CCGAGC-CGATGACTTACTGG-3'; SEQ ID NO: 9) and HSV tk-R (5'-GTCGAAGATGAGGGTGAGGG-3'; SEQ ID NO: 10), Kana-F (5'-ACTGGGCACAACAGACAATC-3'; SEQ ID NO: 11) and SMAR-R (5'-TGGAATTTTTTTGTGTGT-TATGGTA-3'; SEQ ID NO: 12) were used to detect human/mouse GAPDH cDNA, HSV tk cDNA/DNA and S/MAR transcripts, respectively. 28S rDNA primers (28sF: gcctcac-gatccttctgacc; SEQ ID NO: 13, and 28sR: aacccagctcacgt-tcccta; SEQ ID NO: 14) capable of amplifying human and mouse 28s rDNA were used for genomic DNA control.

Tumor Histology

Animals were sacrificed by $CO_2$ overdose when tumors reached 2 cm in size or after they were treated with ganciclovir for 14 days. The tumors were removed and fixed overnight in 10% buffered formalin at 4° C. The tumors were processed, embedded in paraffin, and cut into 5 μm sections. Sections were stained with hematoxylin and eosin.

The results of the experiments are now described.

Construction of an Episomal Vector Capable of Tissue-Specific Expression of Target Genes Since replication of S/MAR-based episomal plasmid DNA in mammalian cells during cell division depends on the continuous transcription of the S/MAR sequence (Piechaczek et al., 1999, Nucleic Acids Res 27:426-8; Stehle et al., 2003, Chromosome Res 11:413-21; Manzini et al., 2006, Proc Natl Acad Sci USA 103:17672-7; Jenke et al., 2004, Proc Natl Acad Sci USA 101:11322-7), the S/MAR sequence and target genes must be controlled by different promoters to allow non-constitutive target gene expression. This is impossible with current S/MAR-based episomal vectors because the S/MAR sequence and target gene are controlled by the same promoter. To make an S/MAR-based episomal vector capable of non-constitutive expression of target genes, an attempt to modify the existing S/MAR-based vector pEPI-eGFP (FIG. 1A) was made so that the S/MAR sequence was controlled by the constitutive SV40 promoter. For unknown reasons, the modified plasmid pS/MAR-GFP1 (FIG. 1B) did not maintain an episomal state in CHO cells. Using flow cytometry analysis, it was found that, without G418 selection, only 3% of treated cells remained GFP-positive 5 days after transfection, similar to non-episomal plasmid pEGFP-C2 transfected cells (2.2%), but significantly lower than episomal plasmid pEPI-eGFP-transfected cells (23.5%). After two weeks of culture in the absence of G418, numerous GFP-positive CHO colonies were observed in pEPI-eGFP-transfected cells, while no GFP-positive CHO colonies were observed in pS/MAR-GFP1-transfected cells. Therefore, the SV40 promoter might be incompatible with the S/MAR sequence for unknown reasons.

Figure 1:
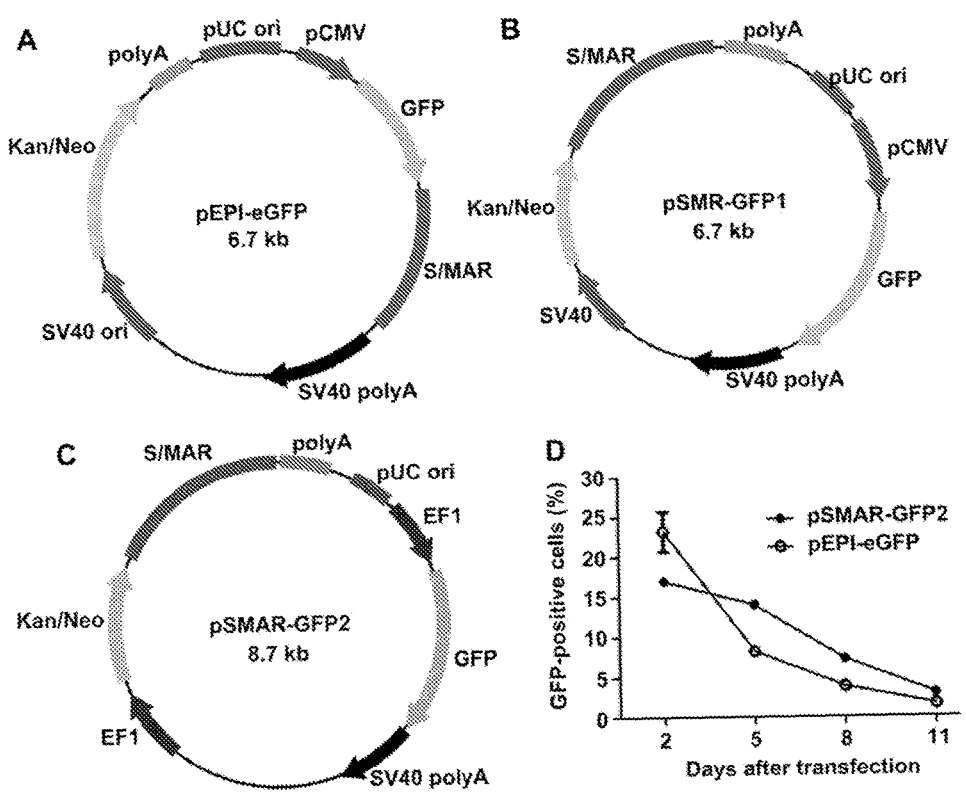
FIG. 1, comprising
Figure 1:
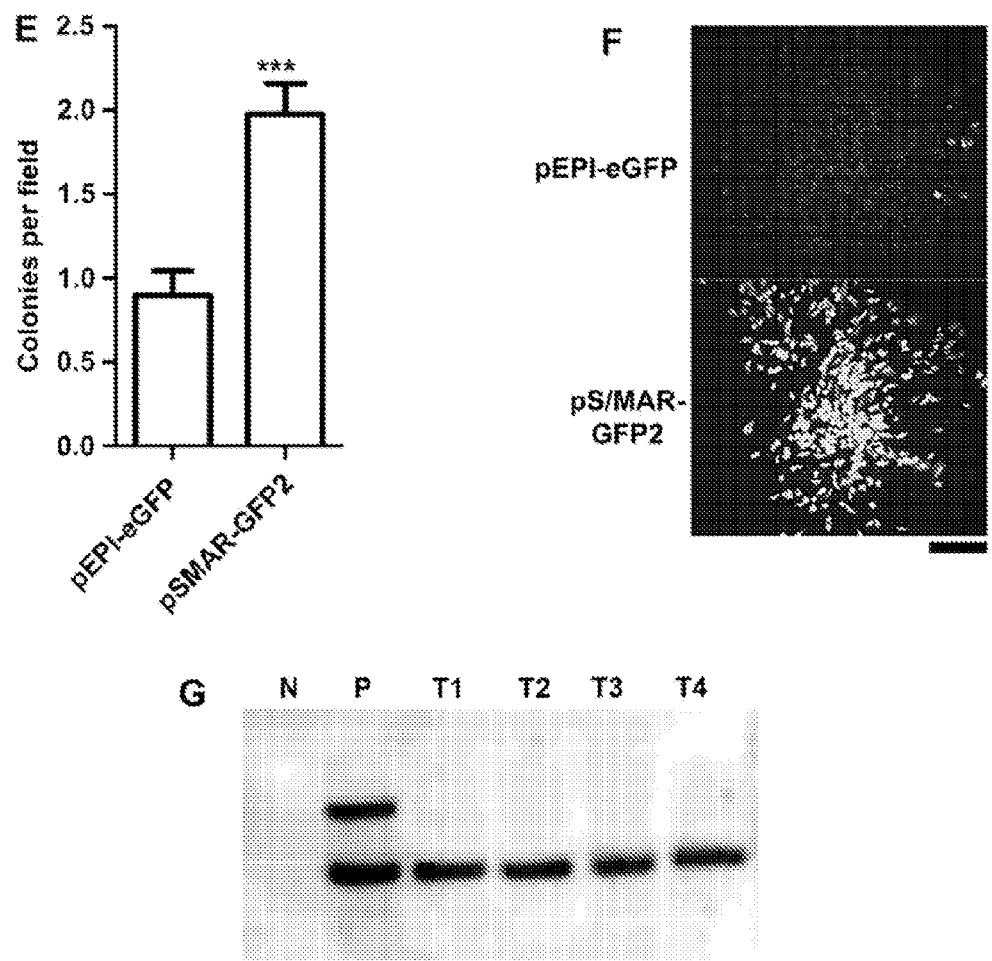

A new construct was made, pS/MAR-GFP2 (FIG. 1C), where the human elongation factor 1α (EF1α) promoter was used to control the transcription of the neomycin selection marker and the S/MAR sequence. The EF1α promoter maintains stable transcription in ES cells before and after differentiation (Norrman et al., 2010, PLoS One 5(8): e12413). The CMV promoter controlling the expression of the reporter GFP gene was also replaced by EF1α promoter, since the CMV promoter is prone to methylation-mediated silencing in human cells in vitro and in vivo (Prosch et al., 1996, Biol Chem Hoppe Seyler 377:195-201; Argyros et al., 2008, Gene Ther 15:1593-605). CHO-K1 cells transfected with pEPI-eGFP or pS/MAR-GFP2 DNA were cultured without G418 selection for 3 weeks and GFP-positive cells were monitored by flow cytometry. Although pEPI-eGFP resulted in more GFP-positive cells 2 days after transfection due to higher transfection efficiency, pS/MAR-GFP2 transfection had higher GFP-positive cells during the subsequent days (FIG. 1D). Both transfections obtained 2-3% GFP-positive cells 11 days after transfection without G418 selection. Flow cytometry analysis was not attempted beyond 11 days since GFP-positive cells were low in both transfections, but this observation is consistent with reports that only 1-5% of cells transfected with pEPI-eGFP establish stable expression and propagation of extra-chromosomal replication (Leight et al., 2001, Mol Cell Biol 21:4149-61; Stehle et al., 2007, BMC Cell Biol 8:33). Three weeks after transfection, pS/MAR-GFP2 resulted in twice as many GFP-positive colonies as pEPI-eGFP (FIG. 1E). In addition, most pS/MAR-GFP2-formed colonies had higher GFP expression than pEPI-eGFP-formed colonies (FIG. 1F).

After pS/MAR-GFP2-derived G418-resistant CHO-K1 clones were propagated in vitro with G418 for more than 20 passages, extra-chromosomal DNA from these cells was isolated with a modified HIRT procedure (Hirt, 1967, J Mol Biol 26:365-9) for Southern blotting analysis with Digoxigenin-labeled pEGFP-C2 DNA as the probe. A band with the same size of pS/MAR-GFP2 plasmid DNA isolated from bacteria was detected in all four pS/MAR-GFP2-positive CHO clones tested, but not in parent CHO-K1 cells (FIG. 1G). An extra band was observed in plasmid DNA isolated from bacteria, which possibly represented different plasmid DNA conformation due to incomplete digestion. Since human interferon-β S/MAR-based plasmids remain as episomal DNA in mammalian cells (Piechaczek et al., 1999, Nucleic Acids Res 27:426-8; Jenke et al., 2004, Proc Natl Acad Sci USA 101:11322-7; Manzini et al., 2006, Proc Natl Acad Sci USA 103:17672-7; Stehle et al., 2003, Chromosome Res 11:413-21), the detection of extra-chromosomal pS/MAR-GFP2 DNA in GFP-positive clones after long-term culture suggests that pS/MAR-GFP2 also maintains an episomal state.

Figure 2:
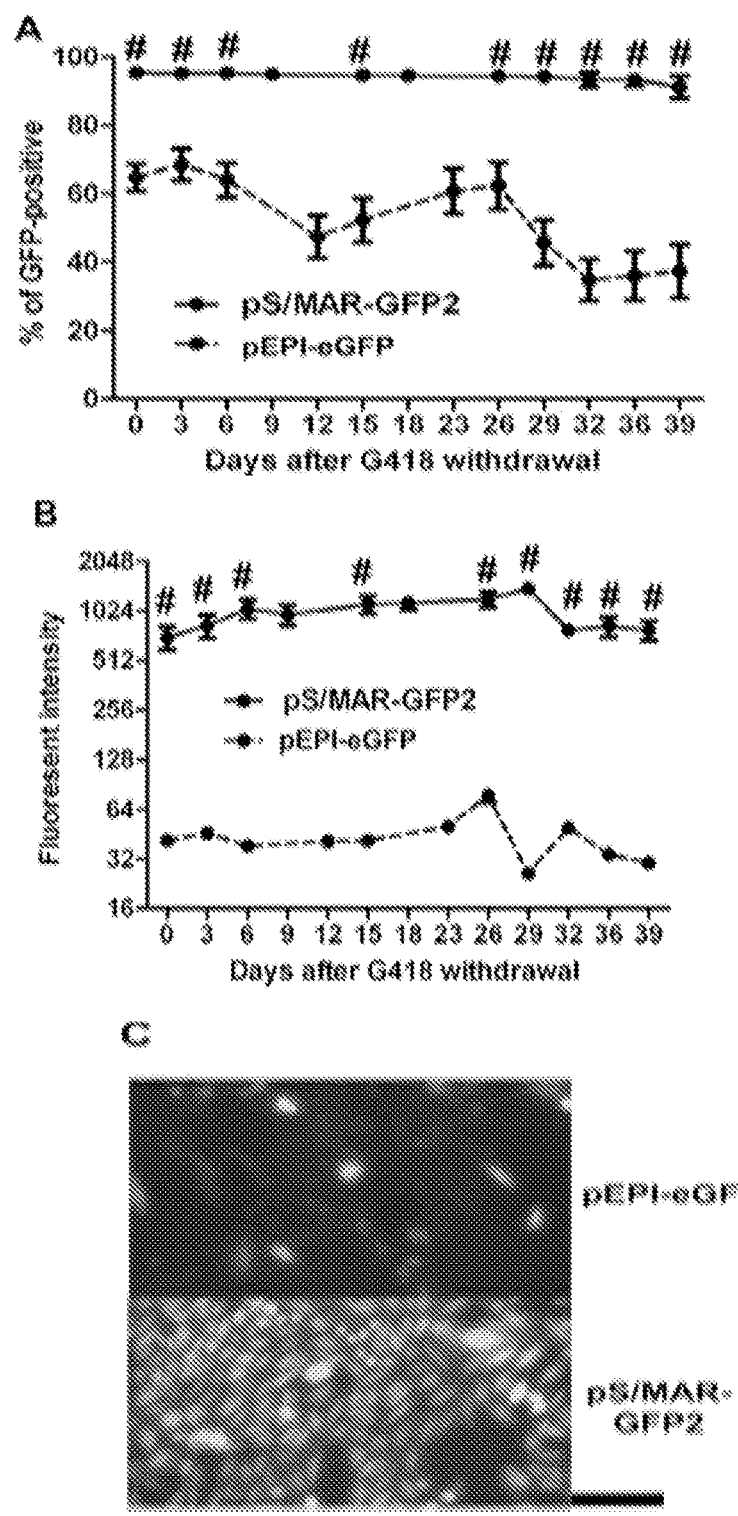
FIG. 2, comprising

The expression of GFP in pS/MAR-GFP2- and pEPI-eGFP-derived G418-resistant CHO-K1 clones was compared after G418 withdrawal. Thirty-nine days after G418 withdrawal (at least 12 passages), GFP-positive cells of eight pS/MAR-GFP2 subclones decreased from 95.4% to 91.1%, while that of nine pEPI-eGFP subclones decreased from 64.8% to 37.4% (FIG. 2A). There was a greater decrease in the percentage of GFP-positive cells in pEPI-eGFP-derived cells than in pS/MAR-GFP-derived cells. Assuming a doubling time of 20 h for CHO-K cells, the data suggest that without G418 selection, about 0.1% of cells lost pS/MAR-GFP2 at every doubling, in contrast to 1.2% with pEPI-eGFP cells. pEPI-eGFP-derived clones showed larger inter-clone variation in percentage of GFP-positive cells. At all time points examined, pS/MAR-GFP2 cells had a significantly higher expression of GFP protein than pEPI-eGFP cells, judged by their average fluorescence intensity (FIG. 2B, 2C). These data demonstrate that pS/MAR-GFP2 outperformed pEPI-eGFP in expression level and stability.

An Episomal Suicide Construct for the Selective Elimination of Pluripotent Stem Cells Since in pS/MAR-GFP2 the S/MAR element and the GFP gene are controlled by their respective promoters, the promoter controlling the GFP gene can be non-constitutive without affecting the episomal maintenance of the construct. To make an episomal suicide construct for the selective elimination of pluripotent stem cells, the EF1α-GFP cassette in pS/MAR-GFP2 was replaced by an OCT4-tk cassette, where the expression of tk cDNA was driven by a 5-kb human OCT4 promoter active only in pluripotent stem cells (Takahashi et al., 2006, Cell 126:663-76). It was suggested that this S/MAR sequence contains a cryptic transcription termination site at approximately 1500-1700 bp (Stehle et al., 2003, Chromosome Res 11:413-21); thus, the possibility of transcription from the EF1α promoter into the OCT4-tk cassette was expected to be minimal. The resultant construct was named pSuicide (FIG. 3A).

To test whether this construct could maintain an episomal state in pluripotent stem cells, the plasmid DNA was transfected into NCCIT cells, a human pluripotent embryonic carcinoma cell line (Teshima et al., 1988, Lab Invest 59:328-36). Extra-chromosomal DNA was extracted by a modified HIRT procedure from G418-resistant clones and analyzed by Southern blotting. A band with the size of pSuicide DNA isolated from bacteria was detected from NCCIT (pSuicide) clones, but not from NCCIT cells (FIG. 3B, left blot). Weak small bands were visible in clone T2 in addition to the expected band but could be eliminated by adjusting the enzyme amount and digestion time before electrophoresis (FIG. 3B, right blot), excluding the existence of episomal plasmid DNA with deletion. As expected, the S/MAR sequence was transcribed (FIG. 3C).

Since TK cDNA is under the control of the human OCT4 promoter in pSuicide, pluripotent NCCIT cells harboring pSuicide episomal DNA are expected to express thymidine kinase, which will convert nontoxic ganciclovir into toxic ganciclovir triphosphate and kill the cells. To test whether this was the case, NCCIT and NCCIT (pSuicide) cells were induced to differentiate in vitro with 20 µmol/L retinoic acid (RA) as described by Damjanov et al. (Damjanov et al., 1993, Lab Invest 68:220-32). Ten days after RA induction, 2 µmol/L ganciclovir was included in the differentiation medium for another 7 days. Without RA-induced differentiation, over 90% NCCIT and NCCIT (pSuicide) cells were positive for OCT4A, a nuclear marker for pluripotent stem cells (Lee et al., 2006, J Biol Chem 281:33554-65). RA induced the differentiation of about 50% NCCIT and NCCIT (pSuicide) cells, resulting in the emergence of cells negative for OCT4A (FIG. 3D, left panels). Addition of ganciclovir did not eliminate OCT4A-positive cells in NCCIT cells (FIG. 3D, upper left), but eliminated OCT4A-positive cells in NCCIT (pSuicide) cells (FIG. 3D, right bottom).

Figure 3:
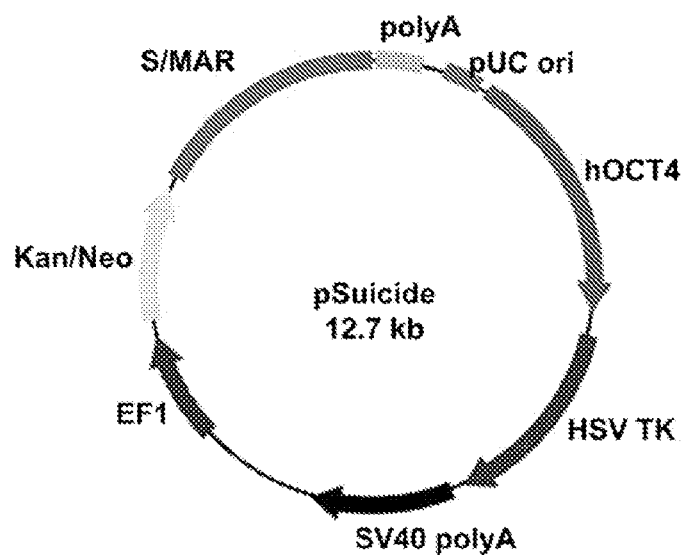
FIG. 3, comprising
Figure 3:
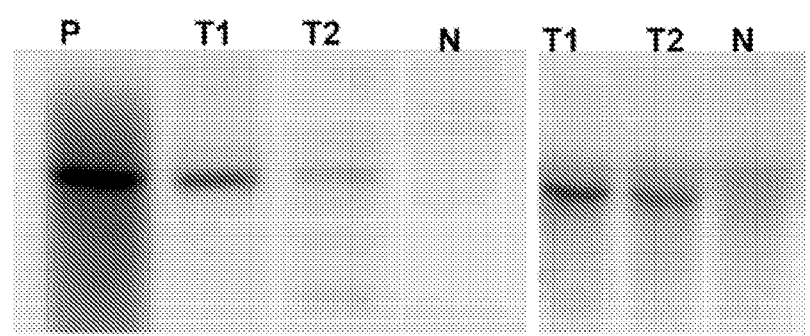
Figure 3:
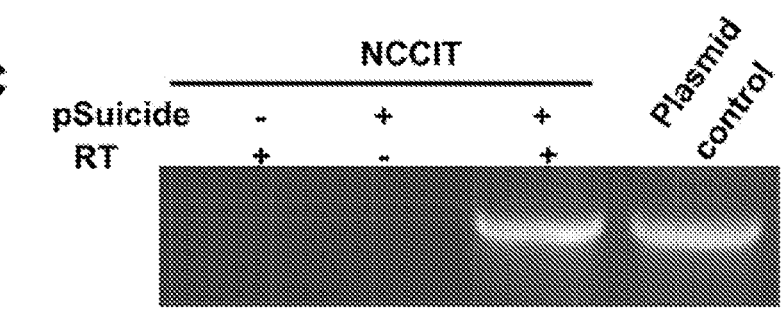
Figure 3:
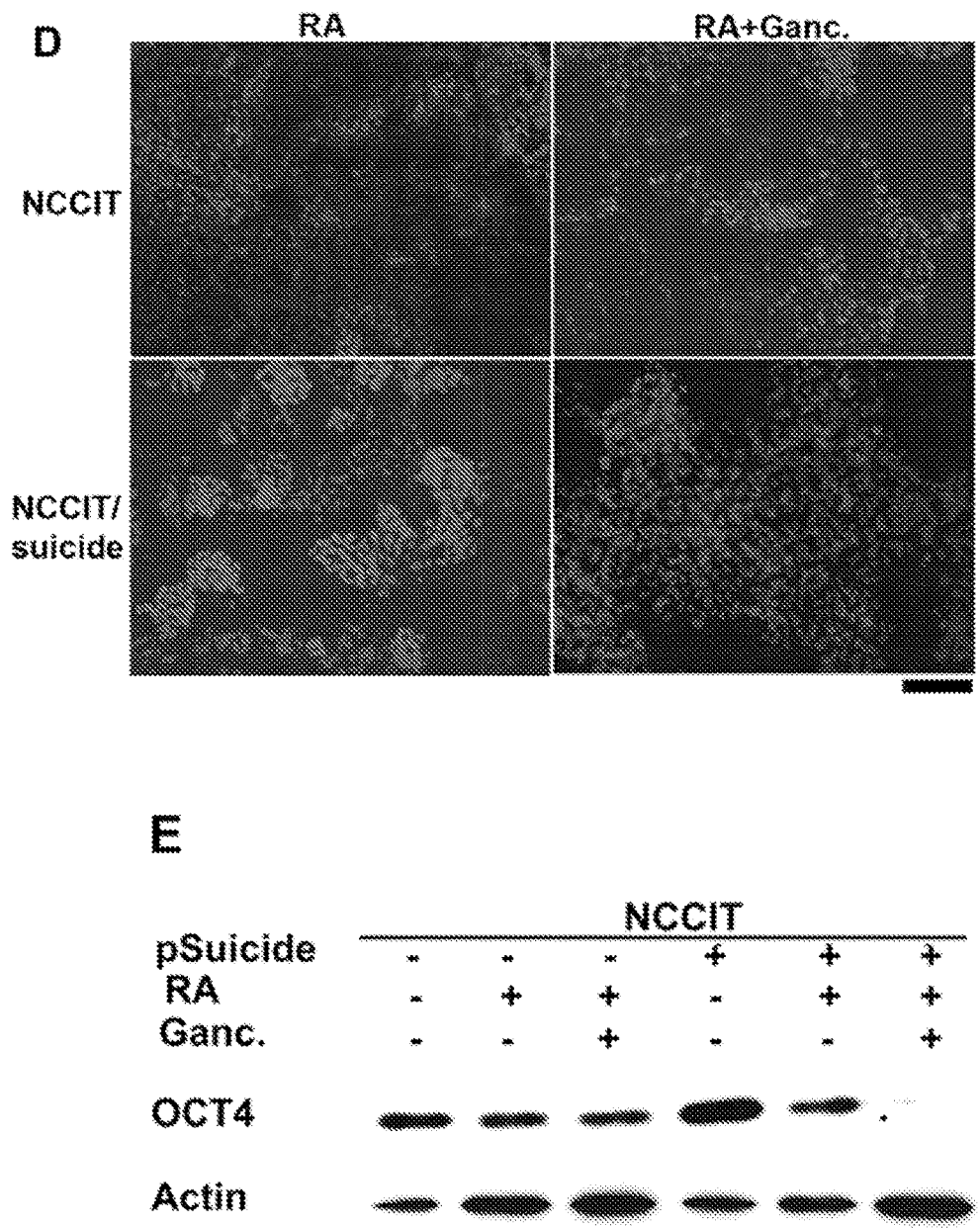
Figure 3:
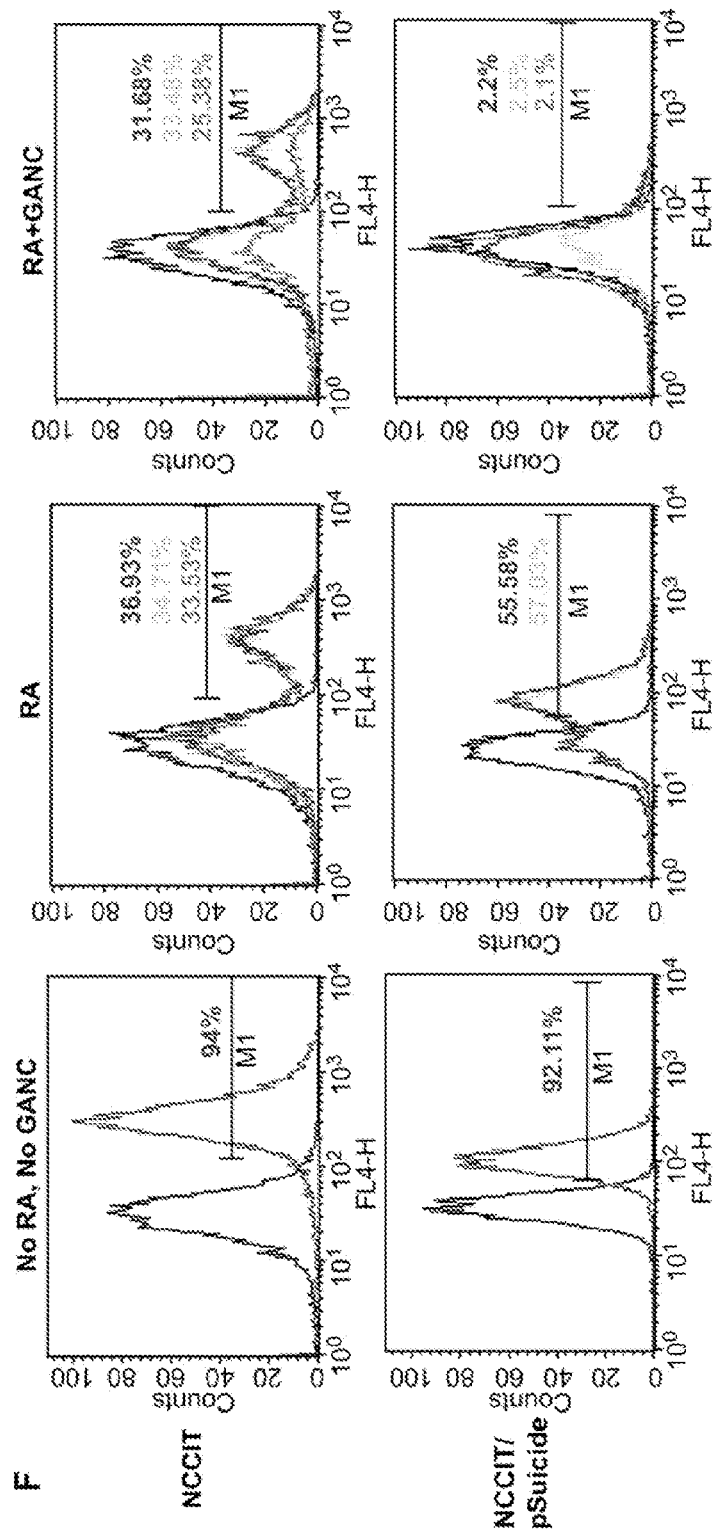

These immunofluorescence data were also confirmed by Western blotting analysis of OCT4A expression in NCCIT and NCCIT (pSuicide) cells under different treatments (FIG. 3E). Addition of ganciclovir to RA-induced NCCIT cells did not reduce OCT4A expression, since it did not reduce the number of OCT4A-positive pluripotent NCCIT cells. However, OCT4A was undetectable after RA-induced NCCIT (pSuicide) cells were treated with ganciclovir, due to the elimination of OCT4A-positive NCCIT (pSuicide) cells. Whereas ganciclovir treatment eliminated OCT4A-positive NCCIT (pSuicide) cells, it did not eliminate differentiated, OCT4A-negative cells in the culture. This observation indicated that tk transcription from the upstream EF1α promoter was minimal at most.

Flow cytometry was performed to quantitatively analyze the effects of ganciclovir treatment on pluripotent stem cells in differentiation cultures. RA induced differentiation in NCCIT and NCCIT (pSuicide) cells; only 40-60% cells were OCT4A-positive, in contrast to over 90% without RA induction (FIG. 3F). Ganciclovir treatment did not significantly affect the percentage of OCT4A-positive cells in RA-treated NCCIT cells (35.06%=1.00% before treatment versus 30.18%±2.46% after treatment), but greatly reduced the percentage of OCT4A-positive cells in RA-treated NCCIT (pSuicide) cells (59.10%±0.5% before treatment versus 2.27%±0.12% after treatment). That 2.27% ganciclovir-treated NCCIT (pSuicide) cells remained OCT4A-positive in flow cytometry analysis was most likely an overestimation, since dead cells with autofluorescence could be erroneously counted as OCT4A-positive cells. In fact, the OCT4A-positive peak completely disappeared in ganciclovir-treated NCCIT (pSuicide) cells. Under a fluorescence microscope, 1670 immunostained, ganciclovir-treated NCCIT (pSuicide) cells were carefully examined; none of these cells showed nuclear staining of OCT4A antibody. Thus, ganciclovir treatment of NCCIT (pSuicide) cells after differentiation significantly decreased residual pluripotent stem cells.

As expected, HSV thymidine kinase protein was detected in NCCIT (pSuicide) cells but not in NCCIT cells (FIG. 4A). Thymidine kinase also was not detected in RA and ganciclovir-treated NCCIT (pSuicide) cells, although the pSuicide plasmid DNA was still detectable in these cells (FIG. 4B). Since pluripotent NCCIT (pSuicide) cells were absent in the RA-differentiated culture after ganciclovir treatment (FIG. 3D) and only differentiated cells were present, inability to detect thymidine kinase protein in these cells further showed that tk gene expression was pluripotent stem cell-specific and tk transcription from the upstream EF1α promoter was minimal. It was noted that although only part of the cells in RA-treated NCCIT (pSuicide) cultures were pluripotent and expected to express thymidine kinase, increased thymidine kinase protein was reproducibly observed in these cells compared to NCCIT (pSuicide) cells without RA treatment (FIG. 4A). Although the endogenous OCT4A gene and the exogenous tk gene were both controlled by the human OCT4 promoter, RA did not seem to increase OCT4A expression in NCCIT (pSuicide) cells (FIG. 3D). It was postulated that RA most likely increased thymidine kinase expression through a post-transcriptional mechanism.

These data demonstrated that pSuicide modification made pluripotent stem cells sensitive to ganciclovir, and addition of ganciclovir to the differentiation culture was able to kill residual pluripotent stem cells but not differentiated cells. However, the mixed culture system described above could not detect whether non-pluripotent cells harboring this construct could still be affected by ganciclovir, even if not killed. To test this, HeLa (pSuicide) and NCCIT (pSuicide) cells were cultured with or without ganciclovir for 7 days. Whereas NCCIT (pSuicide) cells were killed by ganciclovir, HeLa (pSuicide) cells were not (FIG. 4C). In addition, the proliferation of HeLa (pSuicide) cells was not affected by ganciclovir treatment (FIG. 4D). These data confirmed our observations that the pSuicide construct can specifically kill pluripotent stem cells but not differentiated cells in the presence of ganciclovir.

Tumor Control by the Suicide Construct

The ability of the suicide construct to reduce the risk of tumor formation was tested. NCCIT (pSuicide) cells were induced to differentiate by retinoid acid. After differentiation, the cells were treated with or without ganciclovir. $3 \times 10^6$ differentiated cells treated with and without ganciclovir were injected into SCID mice. While 6 of 9 mice injected with untreated cells developed tumors 3 months after injection, only 1 of 12 mice injected with ganciclovir-treated cells did (Table 1). Another two mice injected with ganciclovir-treated cells died for unknown reasons two months after cell injection, but had no tumors. The risk of tumor formation of ganciclovir-treated cells is significantly lower than that of untreated cells. In the single mouse that developed a tumor after injection with ganciclovir-treated cells, pSuicide plasmid DNA was detectable in the tumor but not in the normal liver tissue (data not shown), and the tk cDNA was transcribed (mouse 1 in FIG. 5A).

There are several possible reasons why a tumor formed in this mouse even though the suicide construct was present. First, the cells responsible for tumor formation in this mouse could have escaped in vitro selection due to temporary silencing of the tk gene by methylation. Second, the tumor-forming cells could be partially differentiated, so that they were no more pluripotent and sensitive to ganciclovir in vitro, but were still tumorigenic. For example, neural stem cells are not pluripotent but can form tumors after transplantation (Amariglio et al., 2009, PLoS Med 6(2):e 1000029). Third, the tumor-forming cells might have reverted to pluripotency in vivo due to dedifferentiation and became tumorigenic (Brawley et al., 2004, Science 304: 1331-4). pSuicide plasmid DNA and tk cDNA were also detectable in tumors formed by RA-treated NCCIT (pSuicide) cells without ganciclovir selection (mouse 2 in FIG. 5A).

To examine whether pSuicide modification confers in vivo control of tumors formed from pSuicide-modified cells, the ability of ganciclovir to inhibit the growth of tumors formed by NCCIT (pSuicide) cells was tested. NCCIT (pSuicide) cells and NCCIT cells were injected subcutaneously into immunodeficient SCID mice. The two cell types both formed tumors 6 weeks after cell injection with no significant difference in rate of tumor development (Table 2), indicating that they have similar tumorigenicity. After the size of the tumors reached about 8 mm in any dimension, ganciclovir (50 mg/kg body weight) was injected intraperitoneally daily for two weeks. Whereas all tumors from NCCIT cells continued to grow, all tumors from NCCIT (pSuicide) cells stopped growing after ganciclovir treatment (FIG. 5B). Two of the six mice in Table 1 with tumors after injecting differentiated NCCIT (pSuicide) cells were also treated with ganciclovir, and the tumors of both mice were inhibited by this treatment (FIG. 5B). At the end of ganciclovir treatment, tumors from NCCIT cells were significantly larger than those from NCCIT (pSuicide) cells (FIG. 5C). Histological analysis revealed that NCCIT-formed tumors consisted mainly of undifferentiated cells with large nuclei, which appeared purple on hematoxylin and eosin staining due to minimal eosin staining, while NCCIT (pSuicide)-formed tumors had more differentiated cells and contained regions of low cell density (FIG. 5D).

Safeguarding Pluripotent Stem Cells for Cell Therapy with a Non-Viral, Non-Integrating Episomal Suicide Construct The creation of a S/MAR-based episomal plasmid capable of non-constitutive expression of target genes is disclosed herein. Notably, the transcription of S/MAR sequence found to be necessary for episomal maintenance (Piechaczek et al., 1999, Nucleic Acids Res 27:426-8; Stehle et al., 2003, Chromosome Res 11:413-21; Jenke et al., 2004, Proc Natl Acad Sci USA 101:11322-7; Manzini et al., 2006, Proc Natl Acad Sci USA 103:17672-7) is controlled by the constitutive promoter driving the expression of the neomycin selection marker, but not the target gene. It enables the plasmid DNA to maintain the episomal state no matter whether the target gene is expressed. This has been impossible in previous S/MAR-based episomal vectors, where the transcription of the S/MAR sequence and the target genes are controlled by the same promoter. Here, the episomal vector described herein is used to make a non-integrating suicide construct to specifically eliminate pluripotent stem cells.

Although EBNA-based vectors can remain episomal, they raise safety concerns when used in cell therapy, since EBNA-1 significantly enhances cellular transformation in lymphocytes (Humme et al., 2003, Proc Natl Acad Sci USA 100:10989-94). The human OCT4 promoter and HSV tk gene were used for proof of concept in this work. However, other pluripotent stem cell-specific promoters (for example, hTERT and NANOG promoters) and suicide genes (such as cytosine deaminase (Kievit et al., 1999, Cancer Res 59:1417-21), inducible caspase-9 (Straathofet al., 2005, Blood 105:4247-54), and α-1,3-galactosyltransferase (Hewitt et al., 2007, Stem Cells 25(1):10-8)) should also be compatible with the episomal vector.

The CMV promoter is prone to methylation-mediated silence (Prosch et al., 1996, Biol Chem Hoppe Seyler 377:195-201; Argyros et al., 2008, Gene Ther 15:1593-605), while the human EF1α promoter has a low possibility of being silenced in both pluripotent stem cells and in differentiated cells (Norrman et al., 2010, PLoS One 5(8): e12413). Possibly because human EF1α promoter was used to drive the transcription of S/MAR in pS/MAR-GFP2, it showed more stable gene expression and levels than the prototype episomal plasmid pEPI-eGFP. With improved stability, the data suggest that about 0.1% of the cells will lose pS/MAR-GFP2 at every doubling without G418 selection (in contrast to 1.2% with pEPI-eGFP). It would be desirable to further improve the stability of the episomal plasmid described herein. This can be achieved through the incorporation of the minicircle technique, which will eliminate bacterial-derived sequences and further decrease the chance of transcription silencing by DNA methylation (Argyros et al., 2011, J Mol Med (Berl) 89(5):515-29). However, the possibility of losing the suicide construct without G418 selection will not diminish the value of the episomal suicide construct. The inclusion of G418 during in vitro differentiation will kill any cell that may have lost the suicide construct and ensure that all transplanted cells have the suicide construct. After transplantation, the cells will survive in a G418-free environment, and losing the suicide construct is expected in about 0.1% of transplanted cells. Interestingly, the bystander effect of ganciclovir therapy causes more widespread neighboring cell death than if transgenic cells alone were killed (Dachs et al., 2009, Molecules 14:4517-45); a 1:16 ratio of tk-positive:tk-negative cells was enough for complete tumor eradication (Li et al., 2005, Oncology 69:503-8). Considering that 99.9% of cells will maintain the suicide construct post-transplantation, the likelihood is low that in a tumor formed from transplanted cells, 15/16 (93.75%) of the cells in the tumor have lost the suicide construct. This is also confirmed by experiments showing that all tumors formed from NCCIT (pSuicide) cells tested responded to ganciclovir treatment.

In CHO-K1(pS/MAR-GFP2) cells and NCCIT (pSuicide) cells, extra-chromosomal plasmid DNA was detected after long-term propagation of the cells. This suggests that the plasmid DNA must have established replication with cell division. However, the possibility of spontaneous DNA integration in these cells cannot be ruled out. Due to limited sensitivity of the non-radioactive detection method that was used, it was difficult to detect low copy number integrations. However, radioactive probes have been used by multiple groups to demonstrate the lack of integration in cells harboring the S/MAR-based episomal vectors (Piechaczek et al., 1999, Nucleic Acids Res 27:426-8; Stehle et al., 2003, Chromosome Res 11:413-21; Jenke et al., 2004, Proc Natl Acad Sci USA 101:11322-7; Manzini et al., 2006, Proc Natl Acad Sci USA 103:17672-7). The percentage of cells with integrated DNA in the episome-positive clones, if any, should be low due to the intrinsic low frequency of random integration from circular DNA (Folger et al., 1982, Mol Cell Biol 2:1372-87).

Suicide gene deletion, postinsertional recombination and transgene silencing are potential mechanisms for escape from negative selection in retroviral-mediated suicide gene delivery (Frank et al., 2004, Blood 104:3543-9). With the S/MAR-based episomal suicide construct, extra-chromosomal DNA with reduced size were not detected. In addition, the chance of recombination should be low due to the relatively small size of the construct (about 10 kb). Finally, the S/MAR sequence that was used inhibits de novo methylation and maintains stable long-term expression when incorporated in a retroviral vector (Dang et al., 2000, J Virol 74:2671-8). All these features of the episomal suicide construct suggest that it could be used for genetic modification of pluripotent stem cells. Although NCCIT cells were used in this study, it is highly likely that the episomal suicide construct will function similarly in human embryonic stem cells and iPS cells. Since the episomal status of the suicide construct does not depend on pluripotency, differentiated cells will still harbor the plasmid DNA, as shown by the presence of pSuicide plasmid DNA in RA-differentiated and ganciclovir-treated NCCIT (pSuicide) cells. Furthermore, any possible pluripotent stem cells dedifferentiated from suicide DNA-positive cells will remain so. Thus, the episomal suicide construct of the present invention also offers control of possible tumors from dedifferentiation.

A comparison of the data from the present experimental example with similar published work is difficult due to differences in the cell lines, ganciclovir concentrations and treatment schedules, promoters, and the locations of cells transplanted. As reported by other groups (Schuldiner et al., 2003, Stem Cells 21:257-65; Cheng et al., 2012, Biomaterials 33:3195-204; Jung et al., 2007, Hum Gene Ther 18:1182-92; Naujok et al., 2010, Stem Cell Rev 6:450-61; Hara et al., 2008, Stem Cells Dev 17:619-27; Cao et al., 2006, Circulation 113:1005-14), it was shown that ganciclovir delivery could inhibit the growth of tumors formed by modified pluripotent cells, even though the construct was non-integrating in the present example. Cheng et al. further examined whether ganciclovir treatment before transplantation can reduce the risk of tumor formation (Cheng et al., 2012, Biomaterials 33:3195-204). They observed that cells treated by ganciclovir for 3 and 5 days before transplantation formed tumors with reduced frequency and size. It was shown here that treating cells with ganciclovir for 14 days before injection significantly reduced the chance of tumor development (1/14 from treated cells versus 6/9 from untreated cells). Thus both tests demonstrated that the system of the present experimental example, although non-integrating, was effective in tumor control.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A vector comprising a first nucleic acid comprising a scaffold/matrix attached regions (S/MAR) episomal maintenance element sequence, and a second nucleic acid comprising a suicide gene, wherein the first nucleic acid comprises in 5'-3' order, a constitutive promoter, a gene operably linked to the constitutive promoter, an (S/MAR) sequence and a polyadenylation signal, wherein transcription of the gene operably linked to the constitutive promoter, together with the S/MAR sequence and the polyadenylation signal, is controlled by the constitutive promoter, wherein the second nucleic acid comprises an undifferentiated stem cell specific promoter operably linked to the suicide gene, and wherein expression of the suicide gene is controlled by the undifferentiated stem cell specific promoter, further wherein when the suicide gene is expressed in an undifferentiated stem cell, the undifferentiated stem cell is susceptible to cell death, and wherein the undifferentiated stem cell specific promoter is selected from the group consisting of OCT4, hTERT, and NANOG, and the suicide gene encodes thymidine kinase (TK).

2. The vector of claim 1, wherein the S/MAR episomal maintenance element sequence is capable of long term episomal maintenance of the vector in an entire cell population, and wherein the non-constitutive promoter is capable of expression of the suicide gene in a subset of cells of the entire cell population.

3. The vector of claim 1, wherein the gene operatively linked to the constitutive promoter is Kan/Neo.

4. The vector of claim 1, wherein the undifferentiated stem cell specific promoter is the promoter of OCT4 gene.

* * * * *